(12) United States Patent
Matsuura et al.

(10) Patent No.: US 10,918,302 B2
(45) Date of Patent: Feb. 16, 2021

(54) BIOLOGICAL SIGNAL PROCESSING METHOD AND BIOLOGICAL SIGNAL PROCESSING APPARATUS

(71) Applicant: NIPPON TELEGRAPH AND TELEPHONE CORPORATION, Tokyo (JP)

(72) Inventors: Nobuaki Matsuura, Tokyo (JP); Takayuki Ogasawara, Tokyo (JP); Kei Kuwabara, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 91 days.

(21) Appl. No.: 16/075,116

(22) PCT Filed: Jan. 25, 2017

(86) PCT No.: PCT/JP2017/002483
§ 371 (c)(1),
(2) Date: Aug. 2, 2018

(87) PCT Pub. No.: WO2017/135116
PCT Pub. Date: Aug. 10, 2017

(65) Prior Publication Data
US 2019/0038164 A1 Feb. 7, 2019

(30) Foreign Application Priority Data
Feb. 4, 2016 (JP) .............................. JP2016-019500

(51) Int. Cl.
*A61B 5/0456* (2006.01)
*A61B 5/00* (2006.01)
*A61B 5/0452* (2006.01)

(52) U.S. Cl.
CPC .......... *A61B 5/0456* (2013.01); *A61B 5/0452* (2013.01); *A61B 5/7203* (2013.01); *A61B 5/7235* (2013.01); *A61B 5/7271* (2013.01)

(58) Field of Classification Search
CPC ... A61B 5/0456; A61B 5/0452; A61B 5/7203; A61B 5/7235; A61B 5/7271
(Continued)

(56) References Cited

U.S. PATENT DOCUMENTS

| | | | | |
|---|---|---|---|---|
| 3,848,586 A | * | 11/1974 | Suzuki | A61B 5/0476 600/508 |
| 2004/0092835 A1 | * | 5/2004 | Yasushi | A61B 5/02405 600/513 |

(Continued)

FOREIGN PATENT DOCUMENTS

| | | |
|---|---|---|
| CA | 2565192 A1 | 11/2005 |
| CA | 2807517 A1 | 2/2012 |

(Continued)

OTHER PUBLICATIONS

English Translation of JP2013078543A to Chimura Michihiro; Fukushima Hideki; Itano Kozue; Itao Kenichi; Itao Kiyoshi; Komazawa Masato; Umeda Tomohiro (Year: 2013).*

(Continued)

*Primary Examiner* — William J Levicky
*Assistant Examiner* — Alexander M Eisenberg
(74) *Attorney, Agent, or Firm* — Womble Bond Dickinson (US) LLP

(57) ABSTRACT

There is provided a biological signal processing apparatus. The biological signal processing apparatus includes a biological signal extraction unit (2) configured to extract a biological signal from an electrocardiographic waveform measured by an electrocardiograph (1), an averaging processing unit (3) configured to calculate averaged data using (Continued)

time-series data of the biological signals extracted by the biological signal extraction unit (2), an abnormal value determination unit (4) configured to determine, for each data, whether the data of the biological signal extracted by the biological signal extraction unit (2) is appropriate, based on the averaged data calculated using the data of the biological signals that have occurred before the data, and an abnormal value processing unit (5) configured to perform one of deletion and interpolation of the data of the biological signal determined to be inappropriate by the abnormal value determination unit (4).

15 Claims, 17 Drawing Sheets

(58) Field of Classification Search
USPC .......................................................... 600/521
See application file for complete search history.

(56) References Cited

U.S. PATENT DOCUMENTS

| | | | |
|---|---|---|---|
| 2008/0064964 | A1 | 3/2008 | Nagata et al. |
| 2008/0194978 | A1* | 8/2008 | Beker ................... A61B 5/0472 600/516 |
| 2011/0118618 | A1* | 5/2011 | John .................... A61B 5/4076 600/544 |
| 2012/0197148 | A1 | 8/2012 | Levitan et al. |
| 2012/0310052 | A1* | 12/2012 | Mahapatra ......... A61B 5/04017 600/301 |
| 2015/0150485 | A1 | 6/2015 | Fernando et al. |

FOREIGN PATENT DOCUMENTS

| | | |
|---|---|---|
| CN | 1457246 A | 11/2003 |
| CN | 1933777 A | 3/2007 |
| CN | 101014283 A | 8/2007 |
| CN | 201150533 Y | 11/2008 |
| CN | 102159132 A | 8/2011 |
| CN | 102792336 A | 11/2012 |
| CN | 102846321 A | 1/2013 |
| CN | 103209637 A | 7/2013 |
| CN | 104622446 A | 5/2015 |
| CN | 105030257 A | 11/2015 |
| EP | 1731094 A1 | 12/2006 |
| JP | 2004-337408 A | 12/2004 |
| JP | 2007-535392 A | 12/2007 |
| JP | 2011-098214 A | 5/2011 |
| JP | 2012-065713 A | 4/2012 |
| JP | 2013-078543 A | 5/2013 |
| JP | 2013-532573 A | 8/2013 |
| JP | 2014-168541 A | 9/2014 |
| JP | 5632570 B1 | 11/2014 |
| JP | 2015-156936 A | 9/2015 |
| WO | 2005/082252 A1 | 9/2005 |
| WO | 2005/089645 A1 | 9/2005 |
| WO | 2005/104937 A2 | 11/2005 |
| WO | 2012/017432 A1 | 2/2012 |

OTHER PUBLICATIONS

English Translation of JP2012065713A to Kawamura Yoko; Matsumaru Naoki; Shirai Kunihiro; Yokota Yasunari (Year: 2012).*

International Search Report and Written Opinion received for PCT Patent Application No. PCT/JP2017/002483, dated Apr. 25, 2017, 14 pages (7 pages of English Translation and 7 pages of Original Document).

International Preliminary Report on Patentability received for PCT Patent Application No. PCT/JP2017/002483, dated Aug. 16, 2018, 12 pages (7 pages of English Translation and 5 pages of Original Document).

Chung, Peter, "ECG Implementation on the TMS320C5515 DSP Medical Development Kit (MDK) with the ADS 1298 ECG-FE", Texas Instruments, Application Report, SPRABJ1, Jan. 2011, 20 pages.

Office Action received for Japanese Patent Application No. 2017-565497, dated May 14, 2019, 6 pages (3 pages of English Translation and 3 pages of Office Action).

Minami, Shigeo, "Waveform Data Processing for Scientific Measurement", CQ Publishing, 1986, pp. 173-174.

Mikami, Naoki, "Introduction to Digital Filter and Fast Fourier Transform", CQ Publishing, 2005, pp. 135-137.

Inoue, Hiroshi, "Cardiovascular Disease and Autonomic Nervous Function", Igaku-Shoin, 2010, pp. 85-86.

Office Action received for Japanese Patent Application No. 2017-565497, dated Oct. 29, 2019, 6 pages (3 pages of English Translation and 3 pages of Office Action).

Office Action received for Chinese Patent Application No. 201780009657.6, dated May 29, 2020, 16 pages (6 pages of English Translation and 10 pages of Office Action).

* cited by examiner

処理前　BEFORE PROCESSING
処理後　AFTER PROCESSING
平均　　AVERAGE

処理前 BEFORE PROCESSING
処理後 AFTER PROCESSING

BIOLOGICAL SIGNAL PROCESSING METHOD AND BIOLOGICAL SIGNAL PROCESSING APPARATUS

TECHNICAL FIELD

The present invention relates to a biological signal processing method and biological signal processing apparatus for appropriately removing noise components mixed in biological signals obtained from an electrocardiographic waveform and improving the analysis accuracy of the biological signals.

BACKGROUND ART

It is known that the beating rhythm of a heart fluctuates due to the influence of an autonomic nerve, that is, a sympathetic nerve/vagus nerve. For example, in a resting and relaxed state, the vagus nerve is accentuated, and a heartbeat fluctuation (respiratory sinus arrhythmia) according to respiration is seen conspicuously. The respiratory rate at this time can be estimated by analyzing the time interval between the heartbeat (R wave) times extracted from an electrocardiographic waveform, that is, an R-R interval.

On the other hand, the amplitude of the electrocardiographic waveform is influenced by respiration. The influence on the electrocardiographic waveform amplitude is considered to be exerted when impedance seen from an electrocardiogram measurement system fluctuates due to expansion and contraction of lungs and a thoracic cage according to respiration.

In FIG. 17, (a) is a timing chart showing an example of an electrocardiographic waveform when a subject performs a respiration method called the 4-7-8 breathing method (inhaling for 4 sec-holding breath for 7 sec-exhaling for 8 sec). It can be readily found from (a) of FIG. 17 that the height of the electrocardiographic waveform fluctuates. In FIG. 17, (b) shows a timing chart obtained by extracting data of each R-R interval as the time interval between an R wave and an immediately preceding R wave from the electrocardiographic waveform and time-serially plotting the extracted data. The R-R interval is long at the time of exhaling and short at the time of inhaling (the heart rate is low at the time of exhaling and high at the time of inhaling). It is found from (b) of FIG. 17 that the R-R interval changes in synchronism with the electrocardiographic waveform.

Furthermore, (c) of FIG. 17 is a timing chart obtained by extracting, for each heartbeat, data of an amplitude from the peak value of the R wave to that of the S wave, that is, an RS amplitude and time-serially plotting the extracted data. The RS amplitude can be acquired by, for example, a method of searching for an electrocardiographic waveform in a predetermined section before and after the extracted R wave, and obtaining the difference between the largest and smallest values in the section. It is found from (c) of FIG. 17 that the time width of inhaling-holding breath-exhaling described above appears in the variation pattern of the RS amplitude.

In FIG. 18, (a) is a graph showing a spectrum obtained by analyzing the data of the R-R intervals shown in (b) of FIG. 17 by MEM (Maximum Entropy Method), and (b) is a graph showing a spectrum obtained by analyzing the data of the RS amplitudes shown in (c) of FIG. 17 by MEM. By using MEM, a smooth spectral curve can be obtained even from short data of 60 sec. In the example shown in (a) and (b) of FIG. 18, the spectrum obtained from the RS amplitudes indicates a peak of 19-sec cycle≈0.052 Hz more clearly than the spectrum obtained from the R-R intervals. In this way, it is possible to obtain information about respiration from the RS amplitudes in addition to the R-R intervals.

When measuring an electrocardiographic waveform, noise may be added to the waveform. Especially when acquiring an electrocardiographic waveform in daily life using a portable device or a wearable device, noise is readily mixed due to a body motion or the like. Such noise may also be mixed in the RS amplitude. Furthermore, the noise causes an error in extraction of an R wave, resulting in mixing of inappropriate data in the R-R interval and the like.

Patent literature 1 discloses an arrangement of calibrating a peak value smaller than a predetermined threshold by detecting, based on the predetermined threshold, a case in which no T wave is generated or a case in which the peak value of a T wave is very small in a method of performing respiration estimation based on the peak value of the T wave of an electrocardiographic waveform. In the technique disclosed in patent literature 1, however, when large noise is superimposed on an electrocardiographic waveform, it is impossible to correct a biological signal such as an RS amplitude or R-R interval.

When performing analysis associated with the respiration of a subject or the like based on biological signals such as RS amplitudes or R-R intervals, attention is paid to variation components of the biological signals synchronized with the respiration or the like. A method of applying MEM or a spectrum analysis method such as FFT (Fast Fourier Transform) to the biological signals to extract information concerning respiration or the like is adopted. However, this poses a problem that when the data string of the biological signals includes an inappropriate value derived from noise or the like, an analysis result deviates from an actual result.

RELATED ART LITERATURE

Patent Literature

Patent Literature 1: Japanese Patent No. 5632570

DISCLOSURE OF INVENTION

Problem to be Solved by the Invention

The present invention has been made in consideration of the above problem, and has as its object to provide a biological signal processing method and biological signal processing apparatus capable of appropriately removing noise components mixed in biological signals such as RS amplitudes or R-R intervals and improving the analysis accuracy of the biological signals.

Means of Solution to the Problem

According to the present invention, there is provided a biological signal processing method including a first step of extracting a biological signal from an electrocardiographic waveform of a living body, a second step of calculating averaged data using time-series data of the biological signals extracted in the first step, a third step of determining, for each data, whether the data of the biological signal extracted in the first step is appropriate, based on the averaged data calculated using the data of the biological signals that have occurred before the data, and a fourth step of performing one of deletion and interpolation of the data of the biological signal determined as inappropriate in the third step.

According to the present invention, there is also provided a biological signal processing apparatus including a biological signal extraction unit configured to extract a biological signal from an electrocardiographic waveform of a living body, an averaging processing unit configured to calculate averaged data using time-series data of the biological signals extracted by the biological signal extraction unit, an abnormal value determination unit configured to determine, for each data, whether the data of the biological signal extracted by the biological signal extraction unit is appropriate, based on the averaged data calculated using the data of the biological signals that have occurred before the data, and an abnormal value processing unit configured to perform one of deletion and interpolation of the data of the biological signal determined as inappropriate by the abnormal value determination unit.

Effect of the Invention

According to the present invention, it is possible to appropriately remove noise components mixed in biological signals and improve the analysis accuracy of the biological signals by determining, for each data, whether the data of the biological signal extracted in the first step is appropriate, based on the averaged data calculated using the data of the biological signals that have occurred before the data, and performing one of deletion and interpolation of the data of the biological signal determined to be inappropriate. The value of the biological signal originally varies, and it is preferable to perform processing based not on a fixed value but on an averaged value of past values in order to determine a case in which an inappropriate data may be mixed.

BEST MODE FOR CARRYING OUT THE INVENTION

First Embodiment

Figure 1:
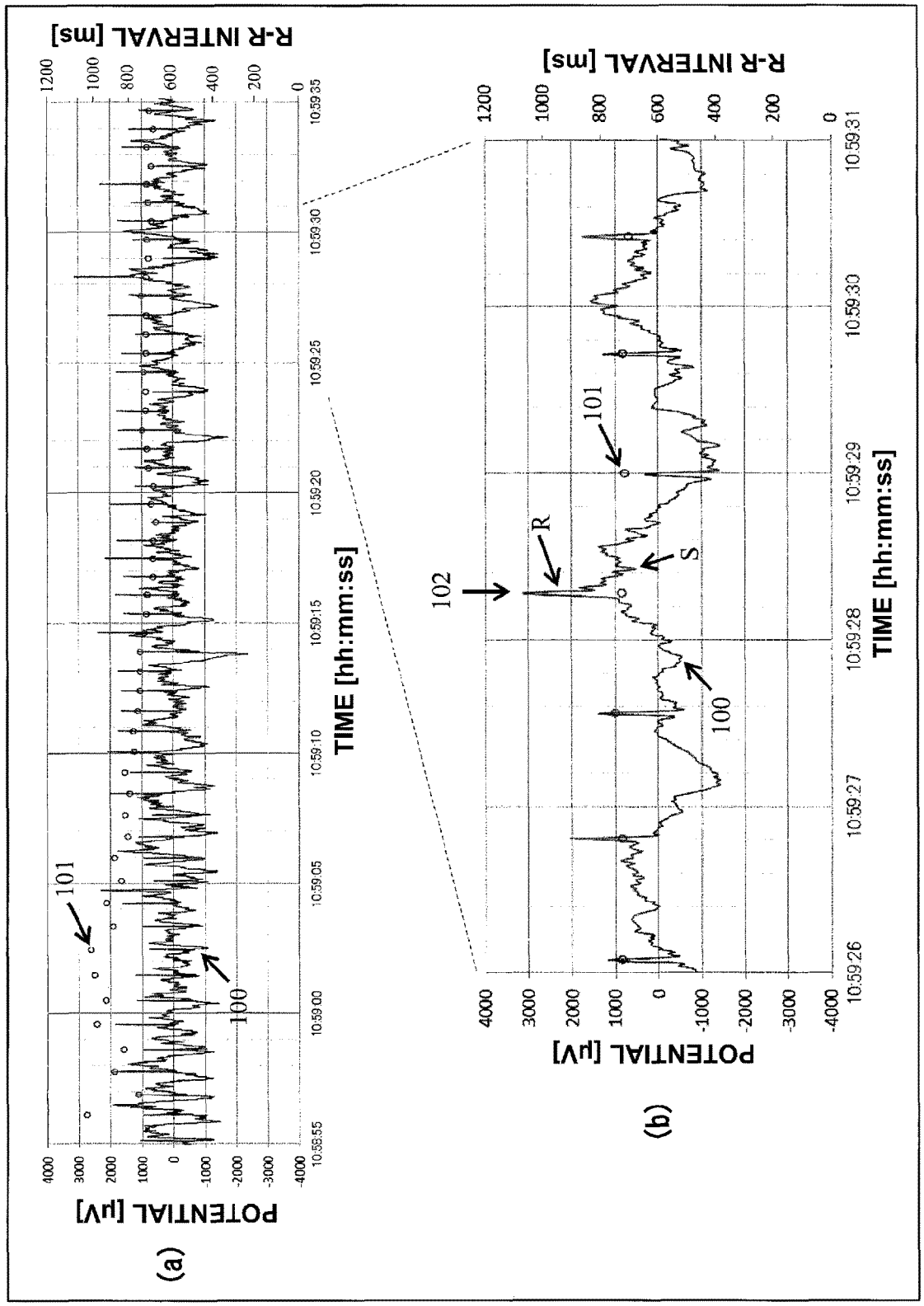
FIG. 1 shows timing charts of examples of an electrocardiographic waveform and time-series data of R-R intervals.

The first embodiment of the present invention will be described with reference to FIGS. 1 to 7. In FIG. 1, (a) is a timing chart showing examples of an electrocardiographic waveform and time-series data of R-R intervals extracted from the electrocardiographic waveform, and (b) is a timing chart obtained by enlarging part of (a) of FIG. 1. In (a) and (b) of FIG. 1, reference numeral 100 denotes an electrocardiographic waveform (unit [µV]); and 101, an R-R interval (unit [ms]). In (a) and (b) of FIG. 1, the abscissa represents the time.

Although noise is superimposed on the electrocardiographic waveform, spikes corresponding to R waves can be confirmed and R-R intervals are extracted correctly. In (b) of FIG. 1 obtained by enlarging (a) of FIG. 1, it is found that at a heartbeat in a portion 102, an R wave overlaps the peak of the noise and an S wave overlaps the slope of the noise.

Figure 2:
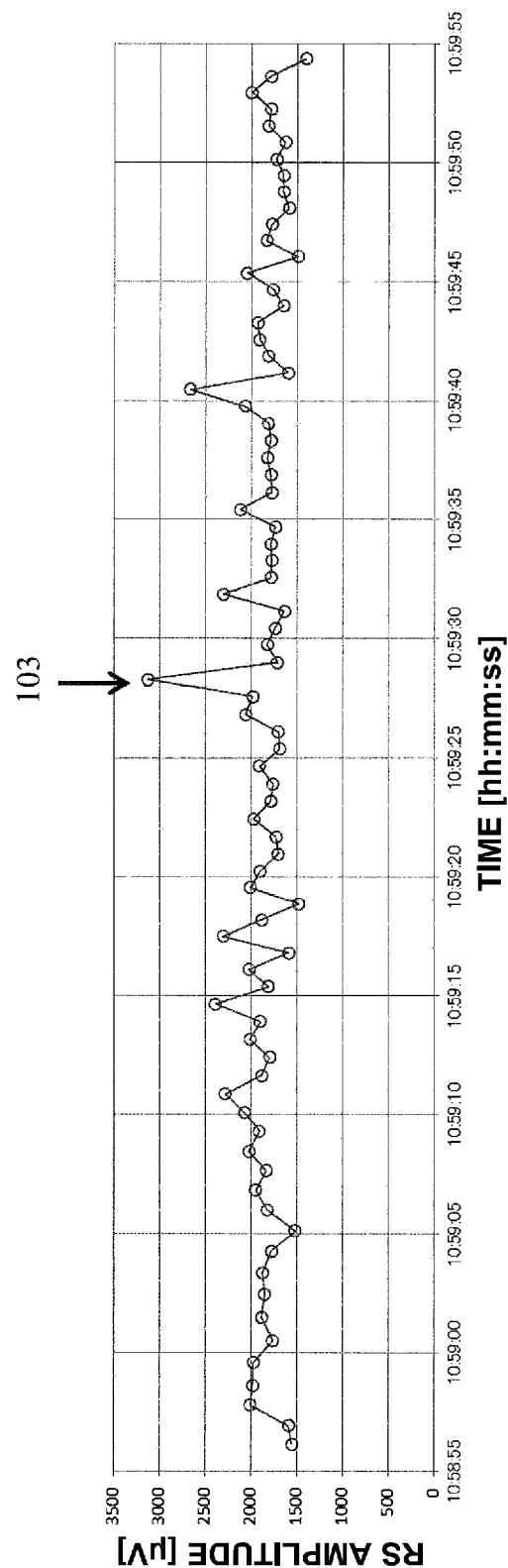
FIG. 2 is a timing chart showing examples of time-series data of RS amplitudes.

FIG. 2 is a timing chart obtained by extracting, for each heartbeat, data of an RS amplitude from the electrocardiographic waveform in (a) of FIG. 1 and time-serially plotting the extracted data. The RS amplitude is calculated from the difference between the largest and smallest values of the electrocardiographic waveform in a section of ±25 ms of heartbeat time. A point in a portion 103 is influenced by the noise, and has an inappropriate value.

Figure 3:
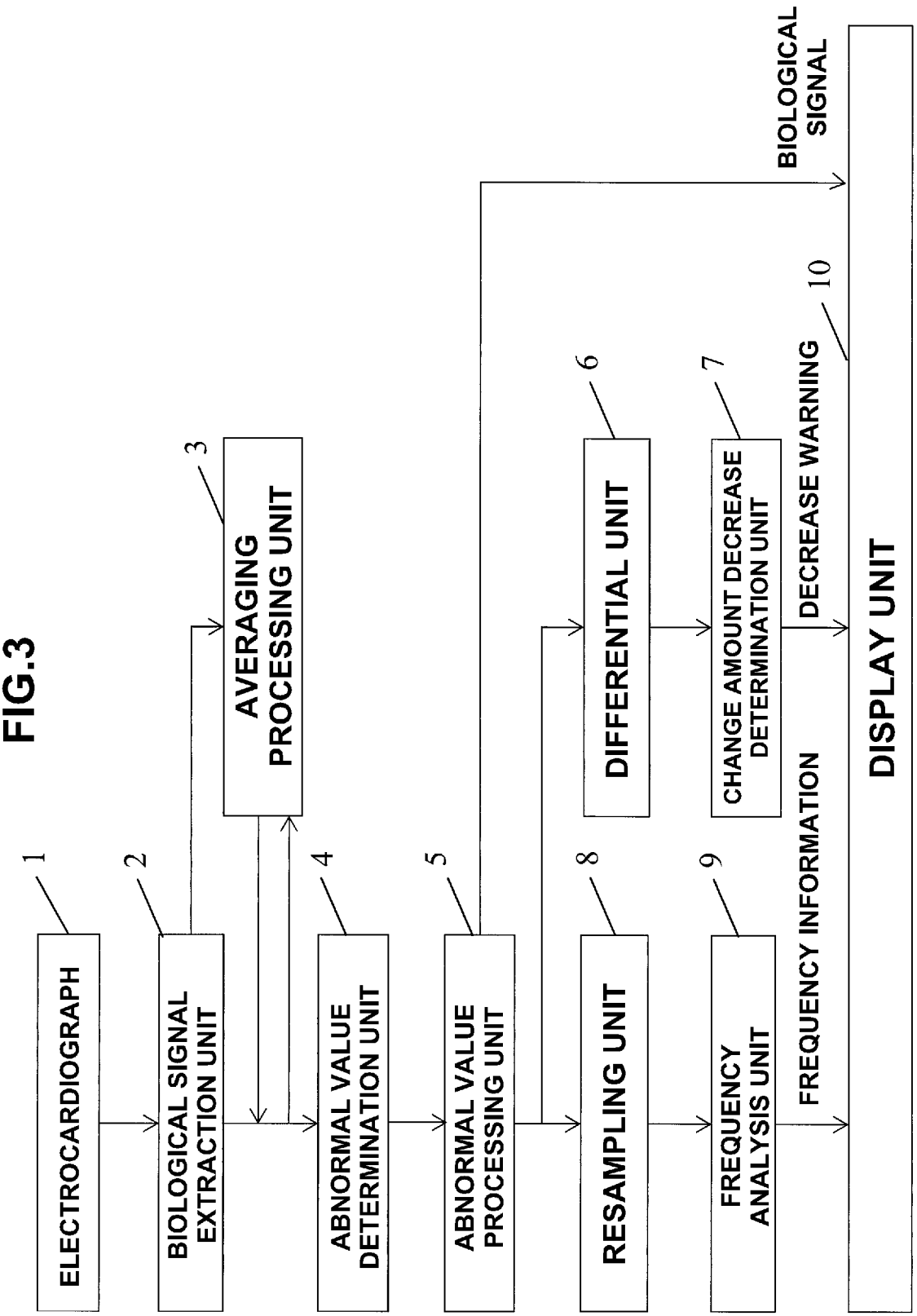
FIG. 3 is a block diagram showing the arrangement of a biological signal processing apparatus according to the first embodiment of the present invention.

FIG. 3 is a block diagram showing the arrangement of a biological signal processing apparatus according to this embodiment. The biological signal processing apparatus includes a biological signal extraction unit 2 that extracts a biological signal from an electrocardiographic waveform measured by an electrocardiograph 1, an averaging processing unit 3 that performs averaging processing for time-series data of the biological signals extracted by the biological signal extraction unit 2, an abnormal value determination unit 4 that compares the data of the biological signal extracted by the biological signal extraction unit 2 with averaged data calculated using the data that have occurred before the data and determines whether the data of the biological signal extracted by the biological signal extraction unit 2 is appropriate, an abnormal value processing unit 5 that deletes the data of the biological signal determined to be inappropriate by the abnormal value determination unit 4 or performs interpolation by replacing the data by appropriate data, a differential unit 6 that calculates the first-order differential value and second-order differential value of each biological signal after the processing by the abnormal value processing unit 5, a change amount decrease determination unit 7 that determines, based on the first-order differential values and the second-order differential values, whether variations in the biological signals are low, a resampling unit 8 that samples the time-series data of the biological signals processed by the abnormal value processing unit 5, a frequency analysis unit 9 that obtains a spectrum of the biological signals by performing frequency analysis of the time-series data of the biological signals acquired by the resampling unit 8, and a display unit 10 that displays the biological signals after the processing by the abnormal value processing unit 5, the determination result of the change amount decrease determination unit 7, and the frequency analysis result of the frequency analysis unit 9.

The operation of the biological signal processing apparatus according to this embodiment will be described next with reference to FIG. 4. In this embodiment, an example in which inappropriate data is removed from the time-series data of the RS amplitudes shown in FIG. 2 will be explained. Note that the operations of the differential unit 6 and change amount decrease determination unit 7 will be described in another embodiment.

The electrocardiograph 1 measures the electrocardiographic waveform of a subject (living body) (not shown). A practical method of measuring an electrocardiographic waveform is a well-known technique and a detailed description thereof will be omitted.

Figure 4:
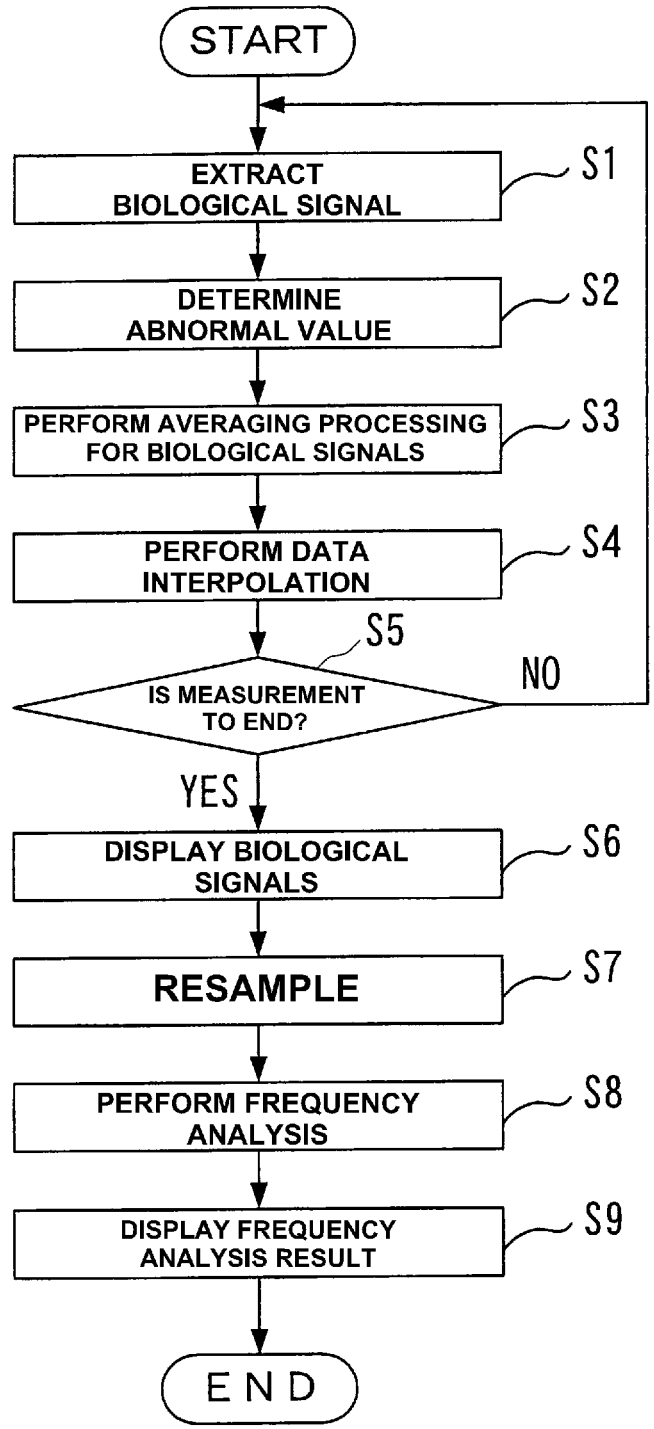
FIG. 4 is a flowchart for explaining the operation of the biological signal processing apparatus according to the first embodiment of the present invention.

The biological signal extraction unit 2 extracts a biological signal (an RS amplitude in this embodiment) from the electrocardiographic waveform measured by the electrocardiograph 1 (step S1 of FIG. 4). For each heartbeat, the biological signal extraction unit 2 according to this embodiment extracts, as an RS amplitude, the difference between the largest value (corresponding to the maximum value of an R wave) of the electrocardiographic waveform and the smallest value (corresponding to the minimum value of an S wave) of the electrocardiographic waveform in a predetermined section (a section of ±25 ms of heartbeat time) centered on heartbeat time.

Note that as a method of obtaining heartbeat time, for example, a technique disclosed in Japanese Patent Laid-Open No. 2015-156936 can be used. In the technique disclosed in this literature, sampling data of two points of the electrocardiographic waveform crossing a predetermined threshold between the representative point of an R wave and the representative point of an S wave existing after that point are detected, and time at which a straight line connecting the sampling data of the two points intersects the threshold is calculated as heartbeat time. This heartbeat time is set as time of the data of the RS amplitude.

The abnormal value determination unit 4 compares the data of the biological signal (RS amplitude) extracted by the biological signal extraction unit 2 with averaged data calculated by the averaging processing unit 3 using the data of the biological signals (RS amplitudes) until immediately preceding time, and determines, for each data, whether the data of the biological signal extracted by the biological signal extraction unit 2 is appropriate (step S2 of FIG. 4).

More specifically, when a value X(i) of the data of the biological signal at given time falls within a predetermined normal value range centered on averaged data X'(i−1) of the biological signals until immediately preceding time, the abnormal value determination unit 4 determines that the data X(i) of the biological signal is appropriate; otherwise, the abnormal value determination unit 4 determines that the data X(i) is inappropriate. In this embodiment, a range of ±30% of the averaged data X'(i−1) is set as a normal value range. Note that since the abnormal value determination unit 4 determines, using the averaged data X'(i−1) of the biological signals of the past times, whether the data X(i) of the biological signal is appropriate, no determination processing is performed for the data of the first biological signal extracted by the biological signal extraction unit 2. The abnormal value determination unit 4 performs the determination processing for the data of the second or subsequent biological signal extracted by the biological signal extraction unit 2.

Next, the averaging processing unit 3 performs averaging processing for the time-series data of the biological signals (RS amplitudes) extracted by the biological signal extraction unit 2 (step S3 of FIG. 4). When X(i) represents the value of the ith biological signal before the averaging processing and X'(i) represents a value obtained by averaging the biological signals up to the ith biological signal, the averaging processing unit 3 performs the averaging processing of the biological signals by:

$$X'(i) = r \times X(i) + (1-r) \times X'(i-1) \quad (1)$$

In equation (1), r represents a predetermined coefficient. As the coefficient r has a smaller value, fine variations in values of the data string of the biological signals are suppressed more but it becomes more difficult to follow rough changes in the biological signals. In consideration of this point, for example, r=0.2 is set, thereby suppressing instantaneous variations in the biological signals, and obtaining an appropriately averaged data string of the biological signals.

To prevent an erroneous value from being mixed in the averaging processing, the averaging processing unit 3 does not use, in the averaging processing, the data of the biological signal (RS amplitude) determined to be inappropriate by the abnormal value determination unit 4. When, for example, the data X(i) of the biological signal is determined to be inappropriate, the averaged data X'(i−1) of the biological signals until immediately preceding time is directly used as averaged data X'(i) without using the data X(i). This can make transition of the value of the averaged data more stable.

The abnormal value processing unit 5 performs interpolation by replacing, by appropriate data, the data of the biological signal (RS amplitude) determined to be inappropriate by the abnormal value determination unit 4 (step S4 of FIG. 4). As an interpolation method at this time, there is provided linear interpolation of performing interpolation for the data of the biological signal determined to be inappropriate using appropriate data before and after the inappropriate data. Instead of linear interpolation, an interpolation method such as spline interpolation may be used.

The biological signal extraction unit 2, the abnormal value determination unit 4, the averaging processing unit 3, and the abnormal value processing unit 5 perform the processes in steps S1 to S4 for every predetermined period (for example, for each sampling operation of the electrocardiograph 1) until, for example, the subject issues a measurement end instruction (YES in step S5 of FIG. 4).

The display unit 10 displays the time-series data of the biological signals (RS amplitudes) processed by the abnormal value processing unit 5 (step S6 of FIG. 4).

Figure 5:
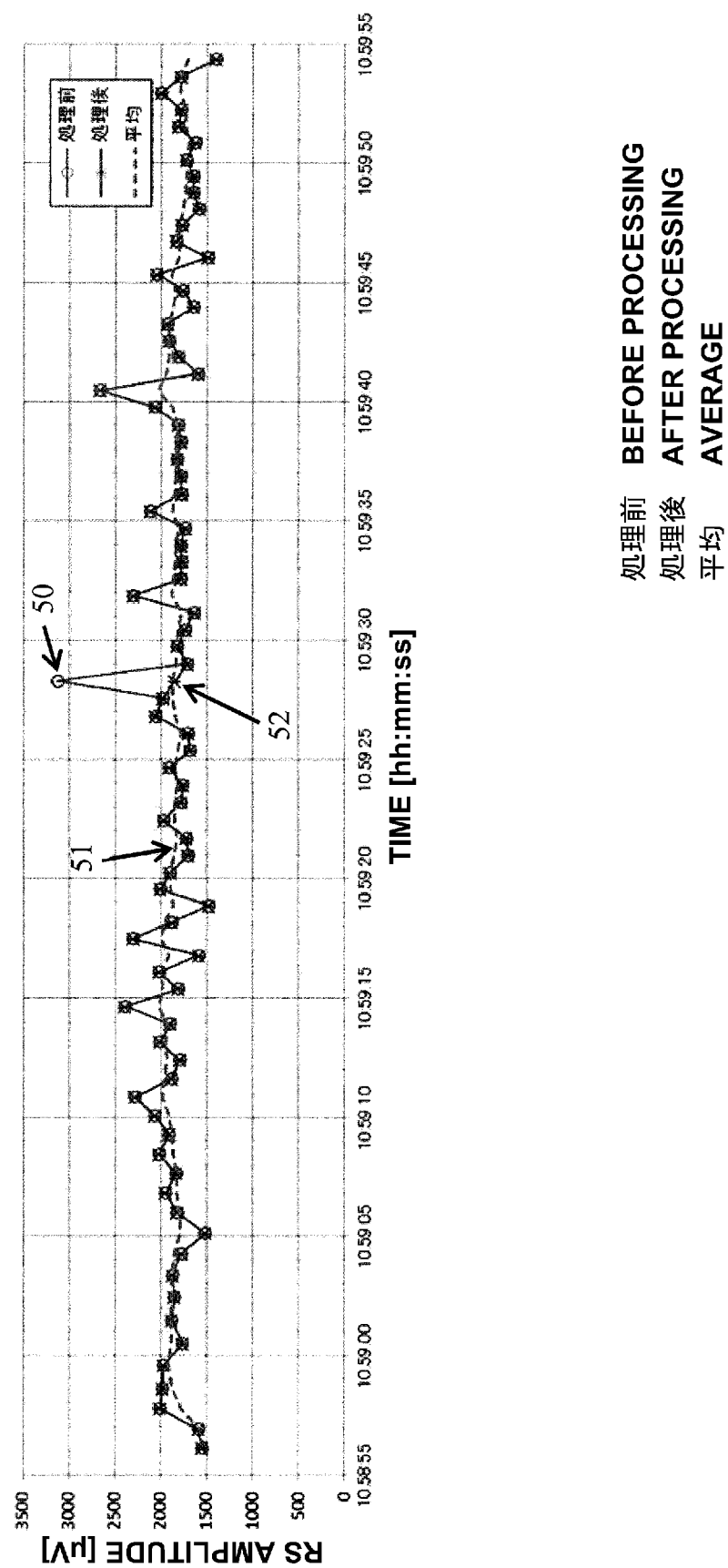
FIG. 5 is a timing chart showing examples of time-series data of RS amplitudes, averaged data of the RS amplitudes, and data of the RS amplitudes after interpolation.

FIG. 5 is a timing chart showing examples of the time-series data of the RS amplitudes, the data obtained by averaging the time-series data of the RS amplitudes by the averaging processing unit 3, and the data of the RS amplitudes after interpolation by the abnormal value processing unit 5. In FIG. 5, "circle" marks 50 indicate the time-series data of the RS amplitudes that are the same as in FIG. 2, a broken line 51 indicates the data obtained by averaging the time-series data, and "cross" marks 52 indicate the data of the RS amplitudes after interpolation. Referring to FIG. 5, it is found that the inappropriate data of the RS amplitude influenced by noise can be interpolated appropriately.

Note that the target of the averaging processing by the averaging processing unit 3 is the data of the biological signals extracted by the biological signal extraction unit 2, and not the data interpolated by the abnormal value processing unit 5, and thus the interpolated data is not used in the subsequent averaging processing. The reason why the interpolated data is not used for the averaging processing is that the interpolated data is data estimated based on the averaged data and thus it is inappropriate to include the interpolated value in the values used to derive the data itself.

The resampling unit 8 samples, at a sampling frequency (for example, an interval of 1 sec) lower than that of the electrocardiograph 1, the time-series data of the biological signals (RS amplitudes) processed by the abnormal value processing unit 5 (step S7 of FIG. 4).

Figure 6:
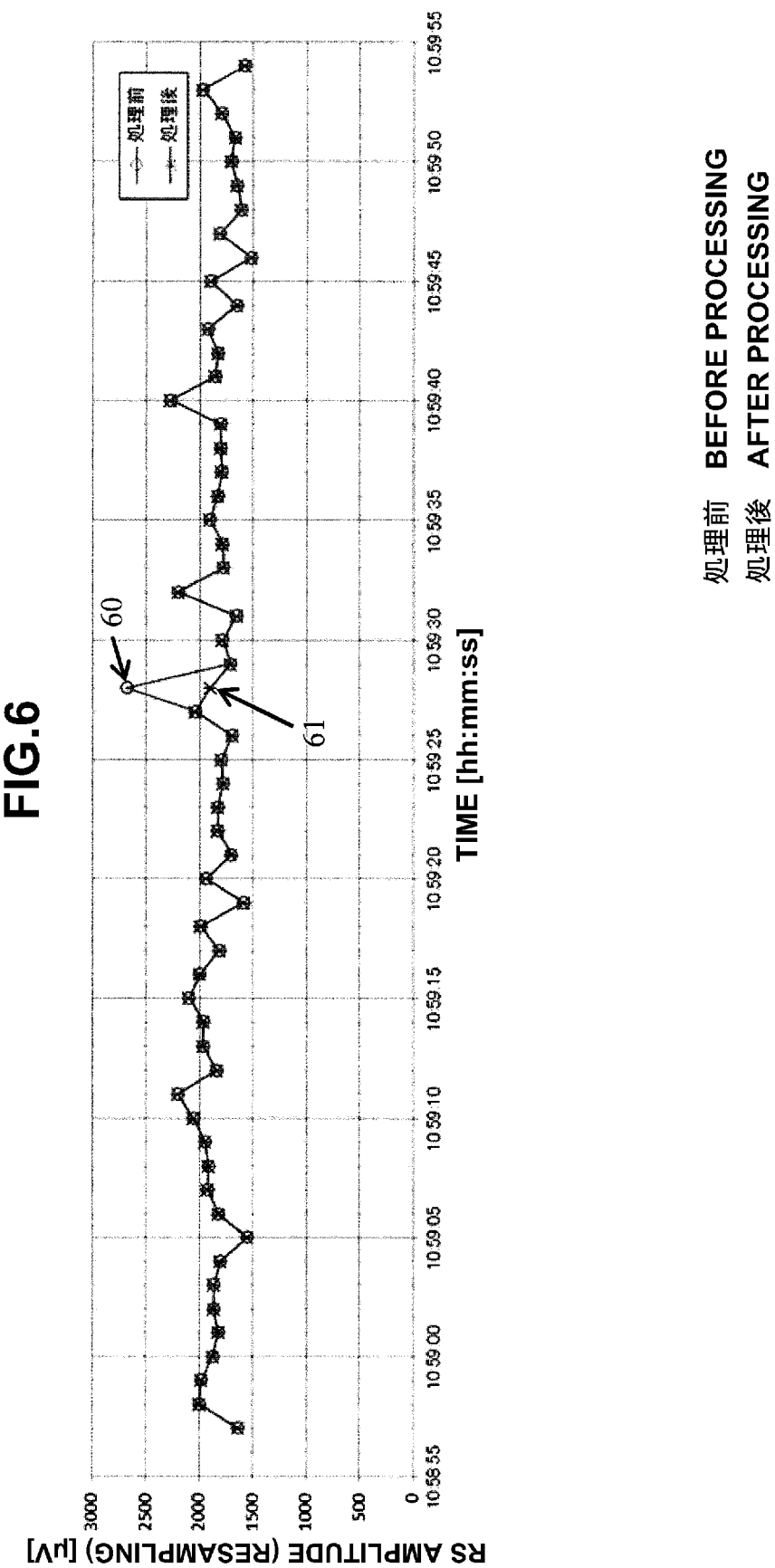
FIG. 6 is a timing chart showing examples of time-series data of the RS amplitudes and data obtained by resampling the time-series data of the RS amplitudes.

FIG. 6 is a timing chart showing examples of the time-series data of the RS amplitudes and the data obtained by resampling the time-series data of the RS amplitudes. In FIG. 6, "circle" marks 60 indicate the time-series data of the RS amplitudes and "cross" marks 61 indicate the data resampled by the resampling unit 8 after interpolation by the abnormal value processing unit 5.

The frequency analysis unit 9 performs frequency analysis for the time-series data of the biological signals (RS amplitudes) acquired by the resampling unit 8 by fast Fourier transform or the maximum entropy method (MEM), thereby obtaining the spectrum of the biological signals (step S8 of FIG. 4).

The display unit 10 displays the spectrum of the frequency analysis result of the frequency analysis unit 9 (step S9 of FIG. 4).

Figure 7:
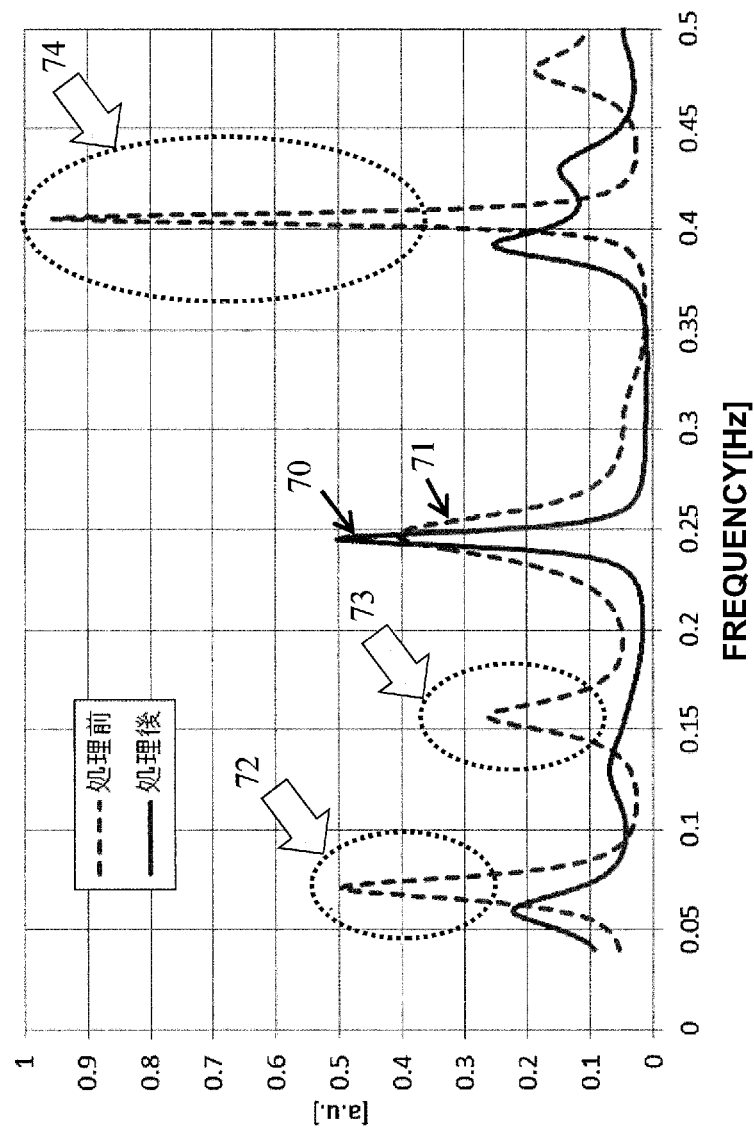
FIG. 7 is a graph showing an example of the spectrum of the RS amplitudes.

FIG. 7 is a graph showing an example of the spectrum obtained by performing frequency analysis by MEM. In FIG. 7, a solid line 70 indicates the spectrum obtained by performing, by MEM, frequency analysis for the time-series data (61 in FIG. 6) of the RS amplitudes acquired by the resampling unit 8. For comparison, a broken line 71 indicates a spectrum obtained by performing, by MEM, frequency analysis for the time-series data (60 in FIG. 6) of the RS amplitudes before the interpolation processing.

The spectrum obtained from the data of the RS amplitudes before the interpolation processing is different in aspect from the spectrum obtained from the data of the RS amplitudes after interpolating the inappropriate data. It is obvious that the spectrum obtained from the data of the RS amplitudes before the interpolation processing includes components or a distribution (72, 73, and 74 of FIG. 7) of the spectrum caused by the inappropriate data. It is considered that the spectrum obtained from the data of the RS amplitudes after interpolating the inappropriate data indicates a result reflecting the state of the living body more correctly.

As described above, in this embodiment, it is possible to appropriately remove noise components mixed in the biological signals such as the RS amplitudes, and improve the analysis accuracy of the biological signals.

Note that in this embodiment, interpolation is performed by replacing, by the plausible data, the data of the biological signal determined to be inappropriate by the abnormal value determination unit 4. However, the present invention is not limited to this. The abnormal value processing unit 5 may delete (data missing) the data of the biological signal determined to be inappropriate by the abnormal value determination unit 4.

Second Embodiment

Figure 8:
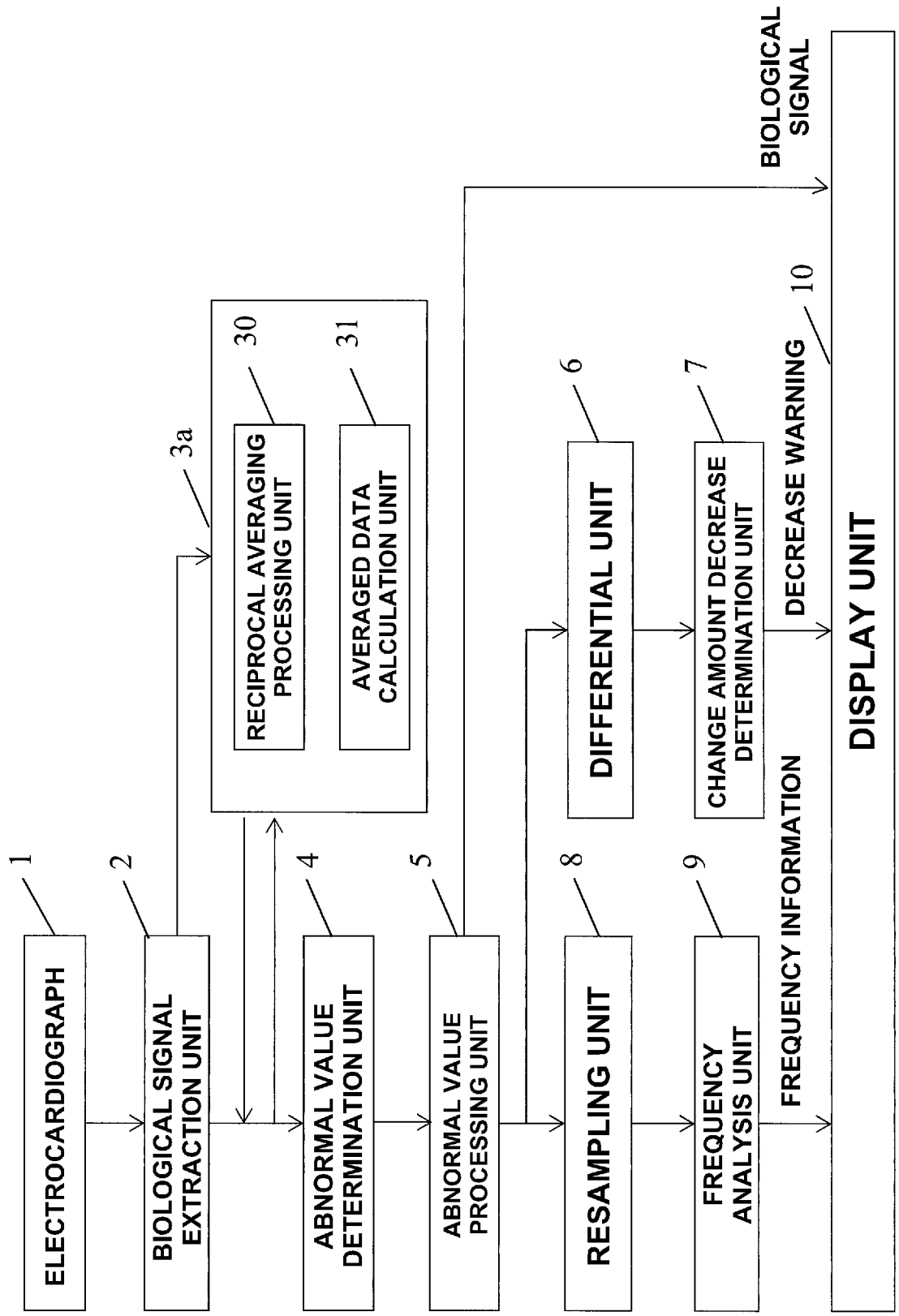
FIG. 8 is a block diagram showing the arrangement of a biological signal processing apparatus according to the second embodiment of the present invention.

The second embodiment of the present invention will be described next. FIG. 8 is a block diagram showing the arrangement of a biological signal processing apparatus according to this embodiment. The biological signal processing apparatus according to this embodiment includes a biological signal extraction unit 2, an averaging processing unit 3a, an abnormal value determination unit 4, an abnormal value processing unit 5, a differential unit 6, a change amount decrease determination unit 7, a resampling unit 8, a frequency analysis unit 9, and a display unit 10. In this embodiment, an example of removing inappropriate data from time-series data of R-R intervals will be described.

The operation of the biological signal processing apparatus according to this embodiment will be described next with reference to FIG. 9. The biological signal extraction unit 2 extracts a biological signal (an R-R interval in this embodiment) from an electrocardiographic waveform measured by an electrocardiograph 1 (step S10 of FIG. 9). As a method of obtaining an R-R interval, for example, it is possible to use a technique disclosed in "ECG Implementation on the TMS320C5515 DSP Medical Development Kit (MDK) with the ADS1298 ECG-FE", Texas Instruments Incorporated, 2011. In the technique disclosed in this literature, an R-R interval is obtained based on a change in value of the time difference of the electrocardiographic waveform. Alternatively, the technique disclosed in Japanese Patent Laid-Open No. 2015-156936 or the like may be used to obtain heartbeat time, and an interval between heartbeat times may be set as an R-R interval.

Figure 9:
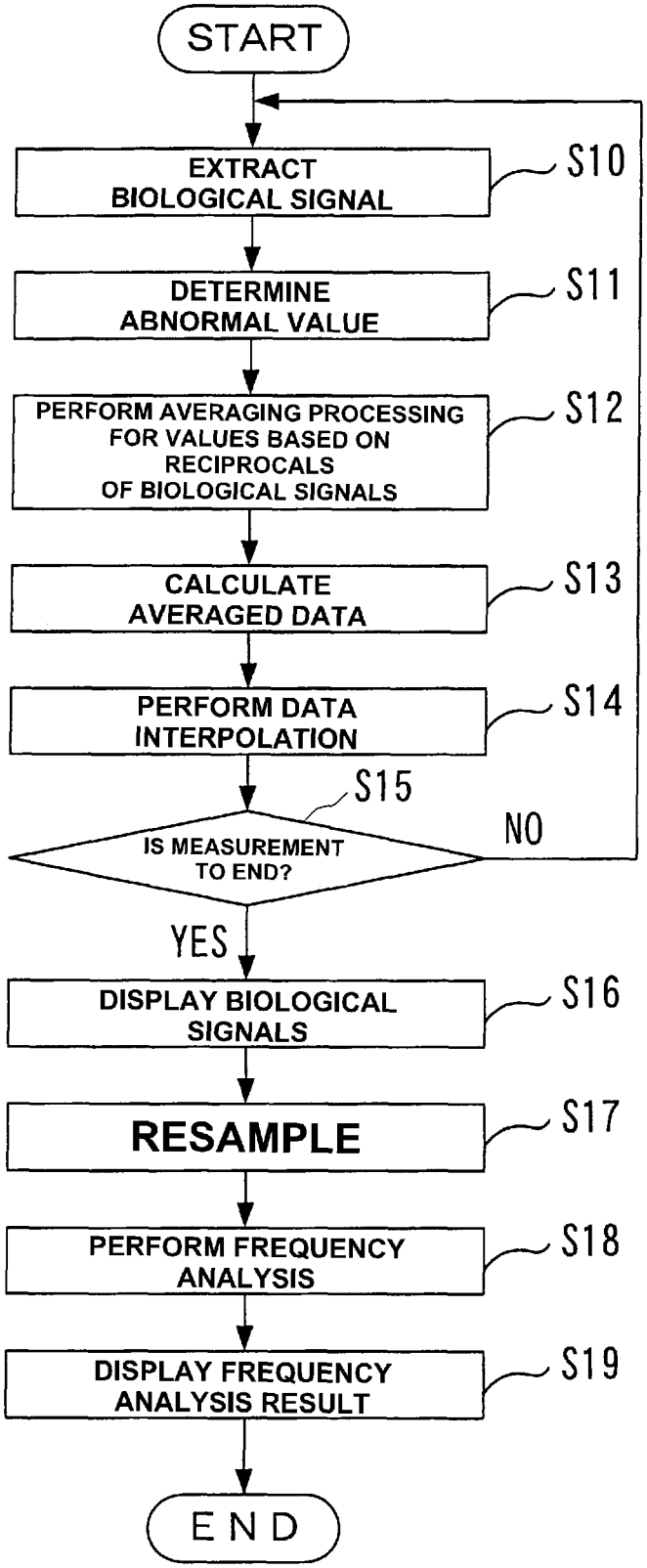
FIG. 9 is a flowchart for explaining the operation of the biological signal processing apparatus according to the second embodiment of the present invention.

The abnormal value determination unit 4 compares data of the biological signal (R-R interval) extracted by the biological signal extraction unit 2 with averaged data calculated by the averaging processing unit 3a using data of the biological signals (R-R intervals) until immediately preceding time, and determines, for each data, whether the data of the biological signal extracted by the biological signal extraction unit 2 is appropriate (step S11 of FIG. 9).

When a value X(i) of the data of the biological signal at given time exceeds a value equal to a predetermined multiple (in this embodiment, 1.35) of averaged data X'(i−1) of the biological signals until immediately preceding time, the abnormal value determination unit 4 according to this embodiment determines that the data X(i) is inappropriate; otherwise, the abnormal value determination unit 4 determines that the data X(i) is appropriate. That is, in this embodiment, a range of the predetermined multiple of the averaged data X'(i−1) or less is set as a normal value range. As described in the first embodiment, the abnormal value determination unit 4 performs the determination processing for the data of the second or subsequent biological signal extracted by the biological signal extraction unit 2.

Next, the averaging processing unit 3a performs averaging processing for the time-series data of the biological signals (R-R intervals) extracted by the biological signal extraction unit 2 (steps S12 and S13 of FIG. 9). The averaging processing according to this embodiment will be described later.

The abnormal value processing unit 5 performs interpolation by replacing, by appropriate data, the data of the biological signal (R-R interval) determined to be inappropriate by the abnormal value determination unit 4 (step S14 of FIG. 9). When the abnormal value determination unit 4 determines that inappropriate data has been generated in the biological signal (R-R interval), the abnormal value processing unit 5 estimates the number (corresponding to a heart rate) of data to be inserted between time when the inappropriate data is generated and immediately preceding time. More specifically, the abnormal value processing unit 5 determines a number N of data to be inserted between time $t_2$ when the inappropriate data is generated in the biological signal (R-R interval) and time $t_1$ of the immediately preceding data by dividing the time interval ($t_2$-$t_1$) between times $t_2$ and $t_1$ by the value of the averaged data of the R-R intervals until time $t_1$.

The abnormal value processing unit 5 calculates, as a plausible value of the R-R interval to be inserted between times $t_2$ and $t_1$, a value obtained by equally dividing the time interval ($t_2$-$t_1$) between times $t_2$ and $t_1$ by the determined number N of data. Thus, the abnormal value processing unit 5 can interpolate the R-R interval by inserting the plausible value of the R-R interval the number N of times between time $t_2$ when the inappropriate data is generated in the R-R interval and immediately preceding time $t_1$.

Figure 10:
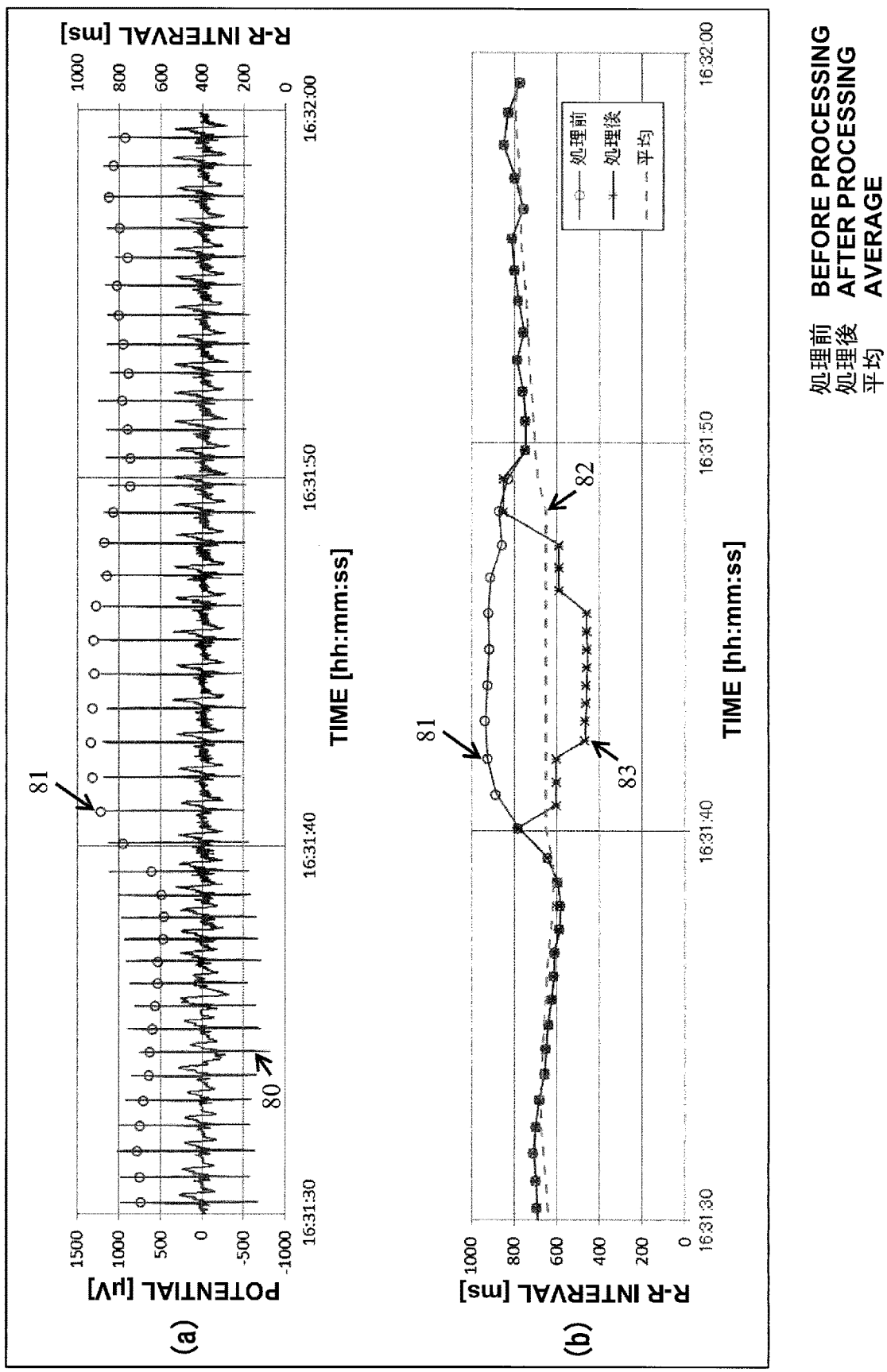
FIG. 10 shows timing charts showing examples of an electrocardiographic waveform, time-series data of R-R intervals, averaged data of the R-R intervals, and data of the R-R intervals after interpolation.

In FIG. 10, (a) is timing chart showing examples of the electrocardiographic waveform and the time-series data of the R-R intervals extracted from the electrocardiographic waveform. In (a) of FIG. 10, reference numeral 80 denotes an electrocardiographic waveform (unit [μV]); and 81, an R-R interval (unit [ms]). In the example shown in (a) of FIG. 10, the R-R interval largely fluctuates near 16:31:40 due to the respiratory motion of the living body.

In FIG. 10, (b) is a timing chart showing examples of the data obtained by averaging the time-series data of the R-R intervals shown in (a) of FIG. 10 and the data interpolated by the abnormal value processing unit 5. In (b) of FIG. 10, a broken line 82 indicates data obtained by averaging the time-series data of the R-R intervals by the method explained in the first embodiment, and "cross" marks 83 indicate the data after interpolation.

In the example shown in (b) of FIG. 10, when obtaining the averaged value of the R-R intervals, the values of the R-R intervals are used to perform averaging processing. To prevent an erroneous value from being mixed in the averaging processing, a value deviating from the averaged value by a predetermined ratio (in this example, ±30% or more) is not used in the averaging processing. However, the value of the R-R interval indicating fluctuation caused by the original state of the living body is regarded as an inappropriate value and is thus not used in the averaging processing, sticking to past values. Then, useless interpolation is continued based on the past values, leading an erroneous result.

To solve this problem, when performing the averaging processing of the biological signals (R-R intervals) extracted by the biological signal extraction unit 2, the averaging processing unit 3a according to this embodiment performs, for each data, an operation of executing the averaging processing for values based on reciprocals of the R-R intervals, and calculating the averaged data of the R-R intervals from the reciprocal of a value obtained by the averaging processing. More specifically, C=60000/R-R interval=heart rate is used as a value (to be referred to as processing target data C hereinafter) based on the reciprocal of the R-R interval. When C(i) represents the ith processing target data, C'(i−1) represents a value obtained by averaging processing target data up to the (i−1)th processing target data, and r represents a predetermined coefficient, a value C'(i) can be obtained by averaging the processing target data up to the ith processing target data, similarly to equation (1), by:

$$C'(i)=r \times C(i)+(1-r) \times C'(i-1) \quad (2)$$

A reciprocal averaging processing unit 30 of the averaging processing unit 3a calculates C'(i) by equation (2) above (step S12 of FIG. 9). Then, an averaged data calculation unit 31 of the averaging processing unit 3a need only calculate averaged data of the R-R intervals by R-R interval=60000/C'(i) (step S13 of FIG. 9).

To prevent an erroneous value from being mixed in the averaging processing, when the processing target data C(i) at given time falls outside a predetermined normal value range centered on the value C'(i−1) obtained by averaging the processing target data until immediately preceding time, the averaging processing unit 3a determines that the processing target data C(i) is inappropriate, and does not use the data in the averaging processing. For example, when it is determined that the processing target data C(i) is inappropriate, the value C'(i−1) obtained by averaging the processing target data until immediately preceding time is directly set as C'(i). A range of ±30% of the averaged data C'(i−1) is set as the normal value range.

Processes in steps S14, S15, S16, S17, S18, and S19 of FIG. 9 are the same as those in steps S4, S5, S6, S7, S8, and S9 of FIG. 4, and a description thereof will be omitted.

Figure 11:
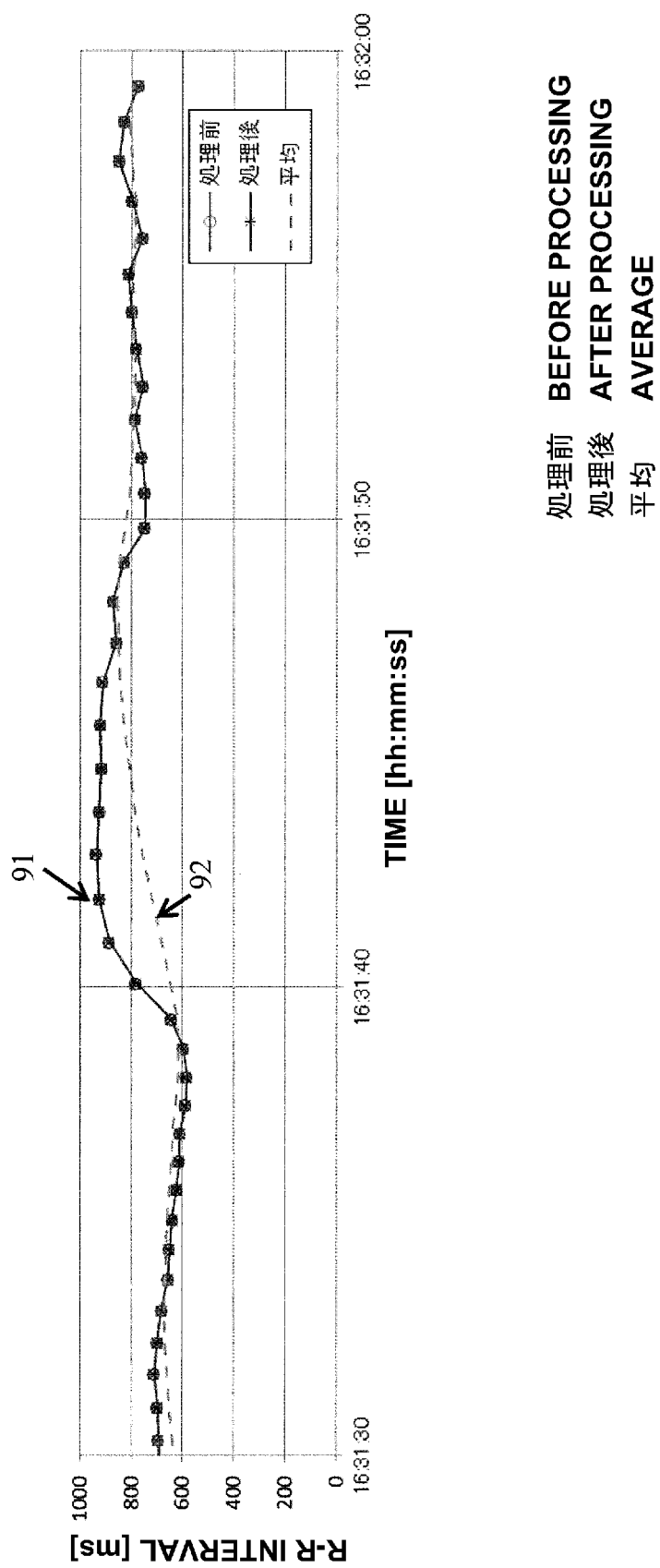
FIG. 11 is a timing chart showing examples of averaged data of the R-R intervals and data of the R-R intervals after interpolation according to the second embodiment of the present invention.

FIG. 11 is a timing chart showing examples of the data obtained by averaging the time-series data of the R-R intervals shown in (a) of FIG. 10 by the method according to this embodiment and the data interpolated by the abnormal value processing unit 5. In FIG. 11, "circle" marks and "cross" marks 91 respectively indicate the time-series data of the R-R intervals and the data of the R-R intervals after interpolation. A broken line 92 indicates the averaged data of the R-R intervals.

While a variation range of the R-R interval in a portion where a variation is most abrupt is a range of about 650 ms→900 ms (variation amount: 42%), a variation range of the heart rate proportional to the reciprocal of the R-R interval is a range of about 92 bpm→67 bpm (variation amount: 27%). Therefore, in the method according to this embodiment, even in a portion where the R-R interval fluctuates, the fluctuations are included in the averaging processing, and thus the data of the R-R intervals having undergone the interpolation processing never deviate from the data of the R-R intervals before the interpolation processing. That is, since the scale of the variation is suppressed by using the heart rate, the averaging processing is stabilized to perform processing correctly for the data string of the biological signals.

When the value of the data of the biological signal varies, in a given numerical value range, it is possible to suppress the variation width of the averaged data and stabilize the averaging processing by performing the averaging processing not for the values of the data but for values based on the reciprocals of the values of the data. According to this embodiment, it is possible to remove inappropriate data caused by noise or the like from the time-series data of the biological signals, and restore the data plausibly, leading to more correct analysis of the state of the living body.

Third Embodiment

The third embodiment of the present invention will be described next. In this embodiment as well, the arrangement of a biological signal processing apparatus is the same as in the first embodiment and reference numerals in FIG. 3 are used to provide a description. This embodiment will describe the operations of a differential unit 6 and a change amount decrease determination unit 7 of the biological signal processing apparatus shown in FIG. 3.

The operation of the biological signal processing apparatus according to this embodiment will be described with reference to FIG. 12. Processes in steps S1 to S6 of FIG. 12 are the same as in the first embodiment.

Figure 12:
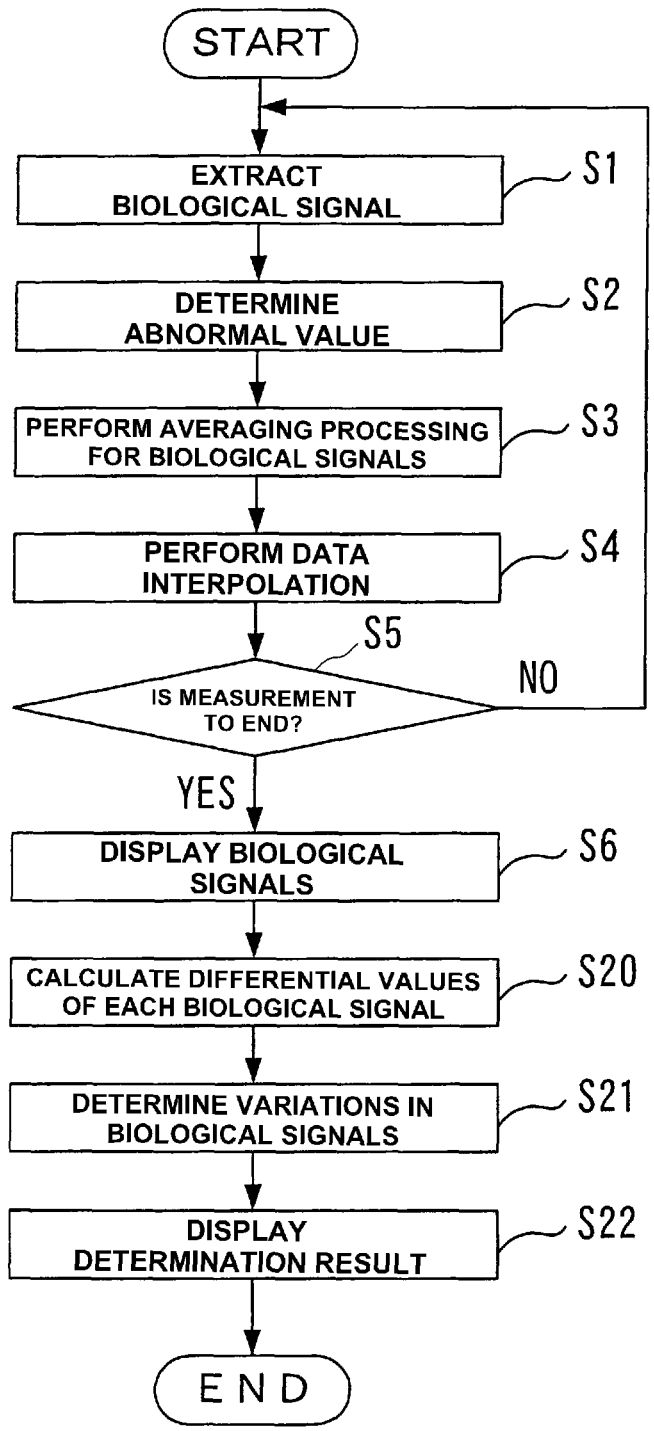
FIG. 12 is a flowchart for explaining the operation of a biological signal processing apparatus according to the third embodiment of the present invention.

The differential unit 6 calculates the first-order differential value and the second-order differential value of each biological signal (RS amplitude) processed by an abnormal value processing unit 5 (step S20 of FIG. 12).

When $f(t_k)$ represents an interpolated value of the biological signal (RS amplitude) at given time $t_k$, a first-order differential value $f'(t_k)$ is given by:

$$f'(t_k)=\{f(t_{k+1})-f(t_k)\}/(t_{k+1}-t_k) \quad (3)$$

Furthermore, a second-order differential value $f''(t_k)$ is given by:

$$f''(t_k)=\{f(t_{k+1})-2f(t_k)+f(t_{k-1})\}/(t_{k+1}-t_k)^2 \quad (4)$$

Since a change in RS amplitude is caused by the respiratory motion, when the respiratory motion stops, for example, when breath is held, both the first-order differential value and the second-order differential value take values close to 0. When a state in which both the first-order differential value and the second-order differential value calculated by the differential unit 6 fall within a predetermined range centered on 0 continues for a predetermined time or longer, the change amount decrease determination unit 7 determines that variations in the biological signals are low (the respiratory motion stops). When at least one of the first-order differential value and the second-order differential value falls outside the predetermined range centered on 0 or the duration of the state in which both the first-order differential value and the second-order differential value fall within the predetermined range is shorter than the predetermined time, the change amount decrease determination unit 7 determines that variations in the biological signals are normal (the respiratory motion changes with time) (step S21 of FIG. 12).

A display unit 10 displays the determination result of the change amount decrease determination unit 7 (step S22 of FIG. 12). This can warn that variations in the biological signals are low. As a warning method, the display unit 10 serving as a notification means may be made to display a warning message, a notification means formed from a light emitting device such as an LED may be additionally provided and made to flicker, or a notification means such as a loudspeaker may be additionally provided and made to give an warning by a sound.

Figure 13:
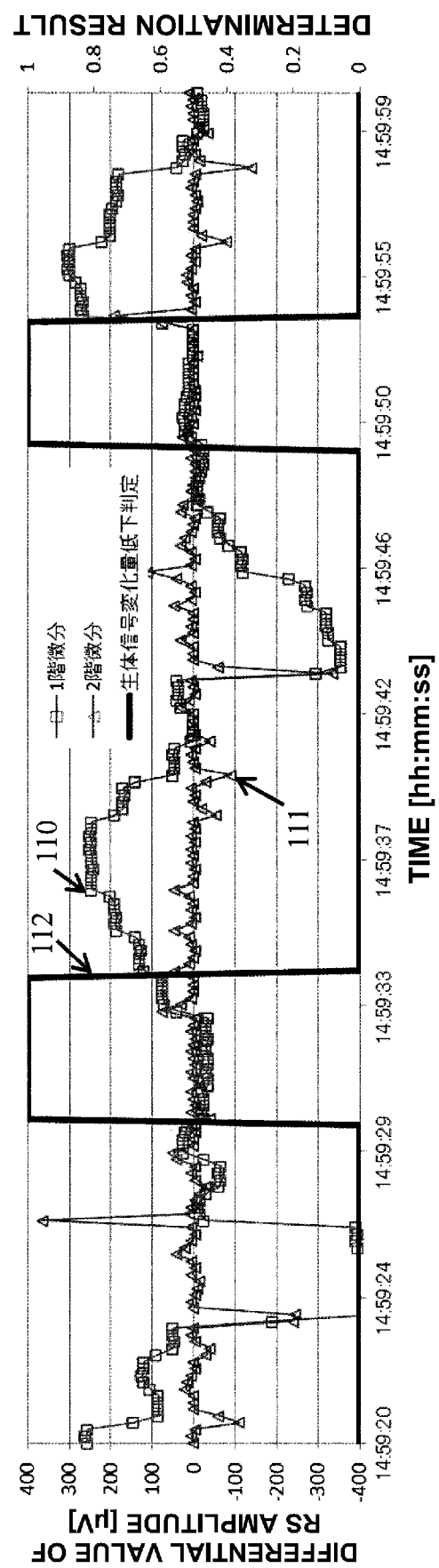
FIG. 13 is a timing chart showing examples of the first-order differential values and second-order differential values of the time-series data of the RS amplitudes and the determination result of a change amount decrease determination unit.

FIG. 13 is a timing chart showing examples of the first-order differential values and second-order differential values of the time-series data of the RS amplitudes shown in FIG. 5 and the determination result of the change amount decrease determination unit 7. In FIG. 13, "square" marks 110 indicate the first-order differential values, "rectangle" marks 111 indicate the second-order differential values, and a solid line 112 indicates the determination result of the change amount decrease determination unit 7.

In the example shown in FIG. 13, when a state in which both the first-order differential value and the second-order differential value fall within a range of ±80 [μV] continues for 3 sec or longer, it is determined that variations in the biological signals are low, and "1" is set as a determination result. When at least one of the first-order differential value and the second-order differential value falls outside the range of ±80 [μV] or the duration of the state in which both the first-order differential value and the second-order differential value fall within the range of ±80 [μV] is shorter than 3 sec, it is determined that variations in the biological signals are normal, and "0" is set as a determination result.

In this embodiment, therefore, it is possible to determine whether the respiratory motion changes with time or stops, thus monitoring the respiratory motion of the living body.

Note that this embodiment has explained the operations of the differential unit 6 and change amount decrease determination unit 7 of the biological signal processing apparatus shown in FIG. 3. However, the same operations can be implemented in the second embodiment shown in FIG. 8 as well.

Fourth Embodiment

The fourth embodiment of the present invention will be described next. In this embodiment, the arrangement of a biological signal processing apparatus and the procedure of processing are the same as in the first embodiment and reference numerals and symbols in FIGS. 3 and 4 are used to provide a description. This embodiment will describe an example of performing frequency analysis for time-series data of RS amplitudes.

As described in the first embodiment, a frequency analysis unit 9 of the biological signal processing apparatus performs frequency analysis for time-series data of biological signals (RS amplitudes) acquired by a resampling unit 8 to obtain a spectrum of the biological signals (step S8 of FIG. 4), and a display unit 10 displays the spectrum (step S9 of FIG. 4).

Figure 14:
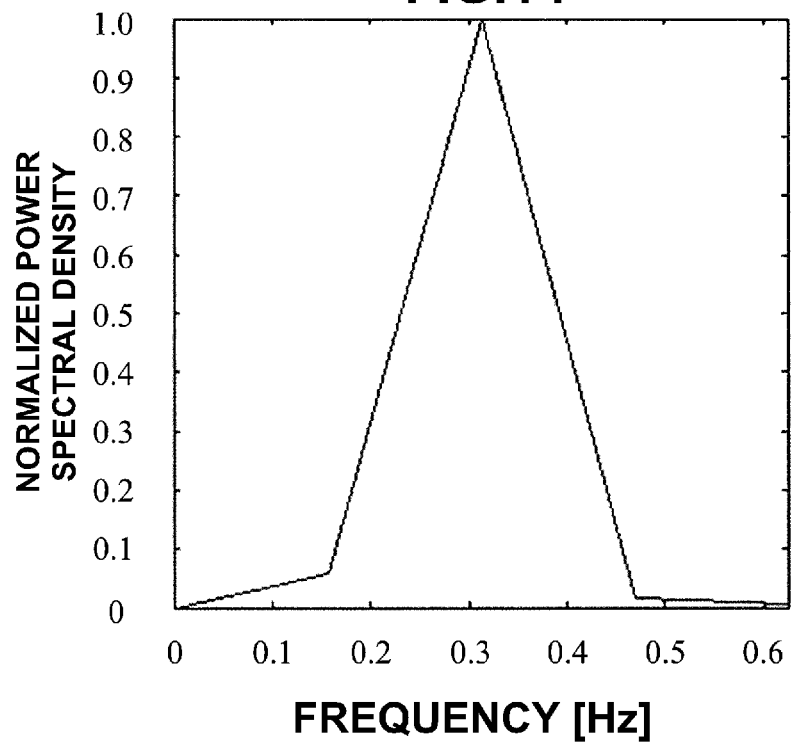
FIG. 14 is a graph showing an example of a spectrum obtained by performing frequency analysis for RS amplitudes by fast Fourier transform according to the fourth embodiment of the present invention.

FIG. 14 is a graph showing an example of the spectrum obtained by performing frequency analysis for the RS amplitudes by fast Fourier transform. The abscissa represents the frequency and the ordinate represents a spectral energy density normalized so that a maximum peak value is 1. By obtaining the frequency distribution, it is possible to grasp a specific frequency band in which components forming the measured RS amplitude exist, and obtain more characteristic findings of a respiratory motion.

In the example of FIG. 14, calculation of Fourier transform is performed based on 32 time-series data of the RS amplitudes that have been sampled at an interval of 0.2 sec, that is, data for 6.2 sec in total. The frequency resolution in fast Fourier transform is defined by:

$$df=1/T(=1/6.4=1/(0.2\times32)\approx0.16) \quad (5)$$

Thus, a plot interval on the abscissa is about 0.16 Hz (see Naoki Mikami, "Introduction to Digital Filter and Fast Fourier Transform", CQ Publishing, pp. 135-137, 2005).

Equation (5) means that the frequency resolution is uniquely determined by the measurement time. To set the frequency resolution to a value higher than 0.16 Hz, there is no way but to prolong the measurement time when the sampling rate of the resampling unit 8 is fixed.

Figure 15:
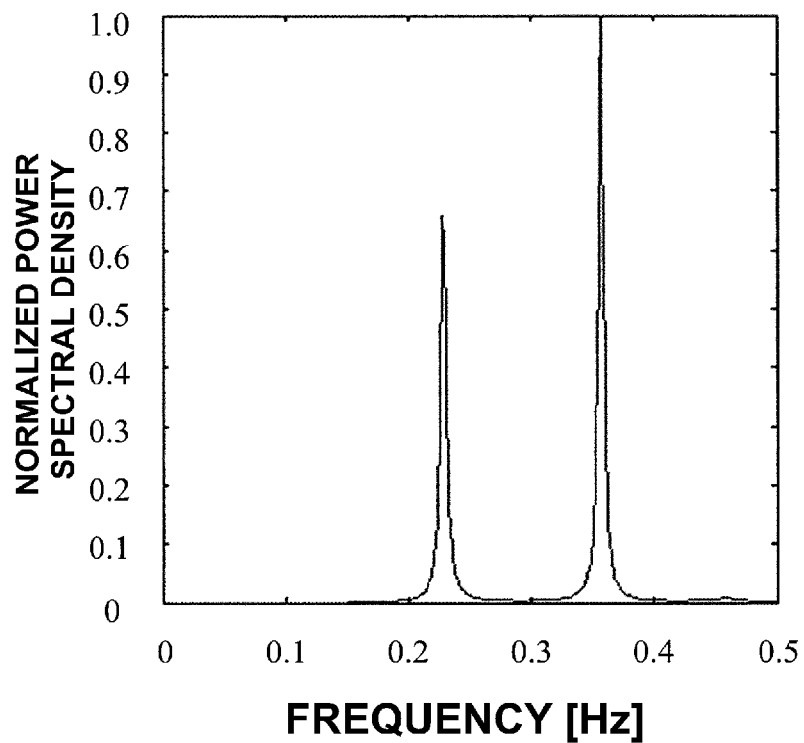
FIG. 15 is a graph showing an example of a spectrum obtained by performing frequency analysis for the RS amplitudes by MEM according to the fourth embodiment of the present invention.

FIG. 15 is a graph showing an example of a spectrum obtained by performing frequency analysis by the maximum entropy method using the data of the same RS amplitudes as in FIG. 14. Unlike fast Fourier transform, in the maximum entropy method, the frequency resolution is irrelevant to the measurement time, and it is thus possible to obtain a high frequency resolution without prolonging the measurement time.

A respiratory cycle at ordinary times is 3 to 4 sec. When the measurement time is prolonged to improve the frequency resolution in fast Fourier transform, data for a plurality of cycles are included, an obtained frequency distribution is given by a statistic of the data, and thus information of a single respiratory motion is buried. However, a high resolution can be obtained within a short measurement time by using the maximum entropy method, thereby obtaining frequency information concerning a single respiratory motion, which is not a statistic.

Referring to FIG. 15, the frequency resolution is improved, as compared to FIG. 14. Therefore, it can be clearly observed that the peak of the respiration frequency is 0.35 Hz, and a peak of 0.23 Hz that cannot be confirmed in FIG. 14 can be detected.

Calculation of a frequency by the maximum entropy method is performed using the following method (see Shigeo Minami, "Waveform Data Processing for Scientific Measurement", CQ Publishing, pp. 173-174, 1986). The maximum entropy method includes the Burg method and Yule-Walker method. The Burg method will be exemplified here.

A spectral energy density $S(\omega)$ to be obtained is given by the following equation.

$$S_{(\omega)} = \frac{P_m \cdot \Delta t}{\left|1 + \sum_{i=1}^{m} a_{mi} e^{j\omega i \Delta t}\right|^2} \quad (6)$$

$\Delta t$ represents the sampling rate, which is 0.2 sec in the example shown in FIG. 15. $\omega$ represents an angular frequency, which has a relationship of $\omega = 2\pi f$ with a frequency f.

To obtain the spectral energy density $S(\omega)$, it is only necessary to know a coefficient $a_{mi}$ of an autoregressive model, a variance $P_m$ of prediction errors, and a model order m to be used. The model order m takes an arbitrary integer. In this example, as the maximum model order, 20 is selected from values equal to or larger than 16 (see Hiroshi Inoue, "Cardiovascular Disease and Autonomic Nervous Function", Igaku-Shoin, pp. 85-86, 2010), and the order m takes a value between 1 and 20.

To obtain the coefficient $a_{mi}$ of the autoregressive model, it is necessary to obtain $a_{mm}$ by equations (7) to (9) below.

$$a_{mn} = -\frac{2\sum_{i=1}^{N-m} b_{mi} b'_{mi}}{\sum_{i=1}^{N-m}(b_{mi}^2 + b'^2_{mi})} \quad (7)$$

$$b_{mi} = b_{m-1i} + a_{m-1m-1} b'_{m-1i} \quad (8)$$

$$b'_{mi} = b'_{m-1i+1} + a_{m-1m-1} b'_{m-1i+1} \quad (9)$$

In equation (7), N represents the number of data of the RS amplitudes, which is 32 in this example. In equations (7) to (9), the initial values of coefficients $b_{mi}$ and $b'_{mi}$ are given by the following equations. $x_i$ represents the ith data among the N data.

$$b_{0i} = b'_{0i} = x_i \quad (10)$$

$$b_{1i} = x_i \quad (11)$$

$$b'_{1i} = x_{i+1} \quad (12)$$

The coefficient $a_{mi}$ of the autoregressive model and the variance $P_m$ of the prediction errors are obtained from the obtained $a_{mm}$ using recursion relations of equations (13) and (14).

$$a_{mi} = a_{m-1i} + a_{mm} a_{m-1m-i} \quad (13)$$

$$P_m = P_{m-1}(1 - a_{mm}^2) \quad (14)$$

$P_0$ used in equation (14) is obtained by equation (15) below by setting $x_{ave}$ as the average value of the data of the RS amplitudes.

$$P_0 = \frac{N + m + 1}{N - m - 1} \cdot \frac{\sum_{i=1}^{m}(x_i - x_{ave})^2}{N} \quad (15)$$

A statistic $Q_m$ for determining the coefficient $a_{mi}$ to be substituted into equation (6) is calculated.

$$Q_m = \left(1 + \frac{m+1}{N}\right)\left(1 - \frac{m+1}{N}\right)^{-1} E_m^2 \quad (16)$$

$$E_m^2 = \sum_{k=m+1}^{N}\left(x_k - \sum_{i=1}^{m} a_{mi} x_{k-1}\right)^2 \quad (17)$$

Using equation (16), $Q_1$ to $Q_{20}$ are calculated for the statistic $Q_m$. Among them, m that gives the smallest statistic $Q_m$ is set as the model order m to be used in equation (6). Calculation may be aborted when a minimum value of the statistic $Q_m$ appears first during calculation up to $Q_{20}$ by incrementing m by one from m=1, and m when $Q_m$ has the minimum value may be used as the model order m in equation (6). When the minimum value of the statistic does not appear even after calculation up to $Q_{20}$, the largest value (in this case, 20) of the candidates of the order is used.

The coefficient $a_{mi}$ of the autoregressive model, the variance $P_m$ of the prediction errors, and the model order m can thus be obtained, thereby obtaining a frequency distribution by equation (6). In FIG. 15, the frequency resolution is set to $\Delta f = 0.001$. That is, the angular frequency $\omega$ is increased from 0 by 0.00628, performing calculation up to 3.14. A high resolution can be obtained, as compared to $\Delta f = 0.16$ in fast Fourier transform.

Fifth Embodiment

In each of the first to fourth embodiments, when data $X(i)$ of the biological signal as a determination target falls outside the predetermined normal value range based on the averaged data $X'(i-1)$ calculated using the data of the biological signals that have occurred before the data $X(i)$, it is determined that the data $X(i)$ of the biological signal as the determination target is inappropriate. However, the determination processing is not limited to this. For example, a range of the average data X'(i−1)±α (α is a predetermined value) may be set as a normal value range.

Furthermore, the abnormal value determination unit 4 according to each of the first to fourth embodiments may calculate a variance $\sigma^2$ obtained from the averaged data calculated using the data X(i) of the biological signal as a determination target and the data of the biological signals that have occurred before the data (the data of the biological signals until immediately preceding time). Then, when the variance $\sigma^2$ falls outside a predetermined normal value range based on a variance $\sigma_p^2$ obtained from averaged data calculated using the data of the biological signals of the past times, the abnormal value determination unit 4 may determine that the data X(i) of the biological signal is inappropriate. For example, a range of $2\sigma_p^2$ or less is set as a normal value range. When the variance $\sigma^2$ exceeds $2\sigma_p^2$, it is determined that the data X(i) of the biological signal is inappropriate.

Sixth Embodiment

Figure 16:
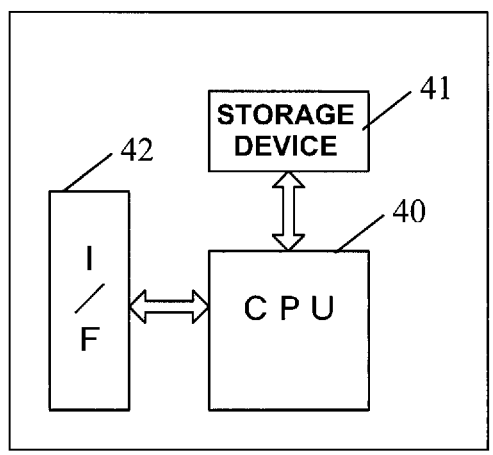
FIG. 16 is a block diagram showing an example of the arrangement of a computer for implementing the biological signal processing apparatus according to the first to fifth embodiments of the present invention.
Figure 17:
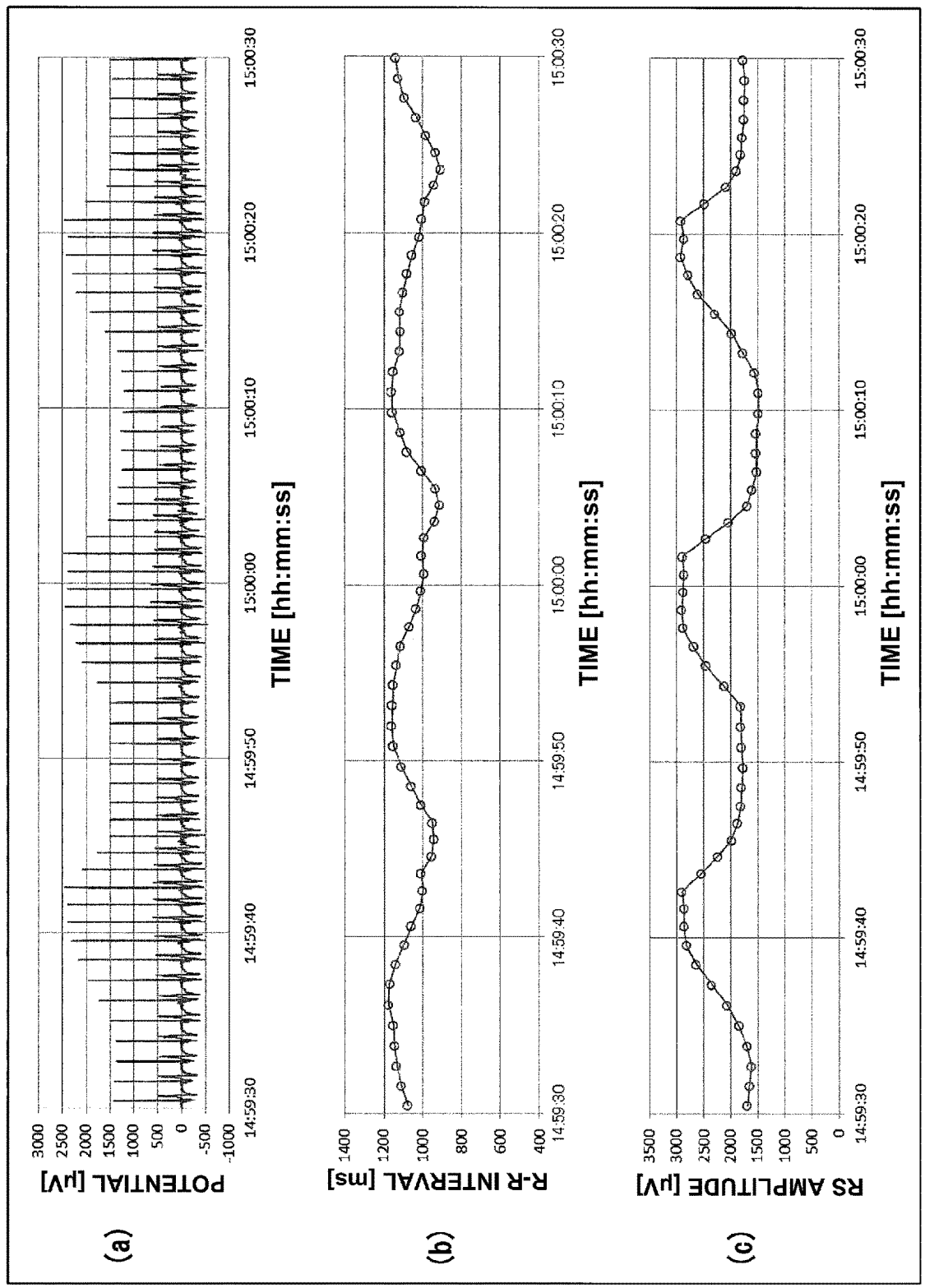
FIG. 17 shows timing charts showing examples of an electrocardiographic waveform, time-series data of R-R intervals, and time-series data of RS amplitudes.
Figure 18:
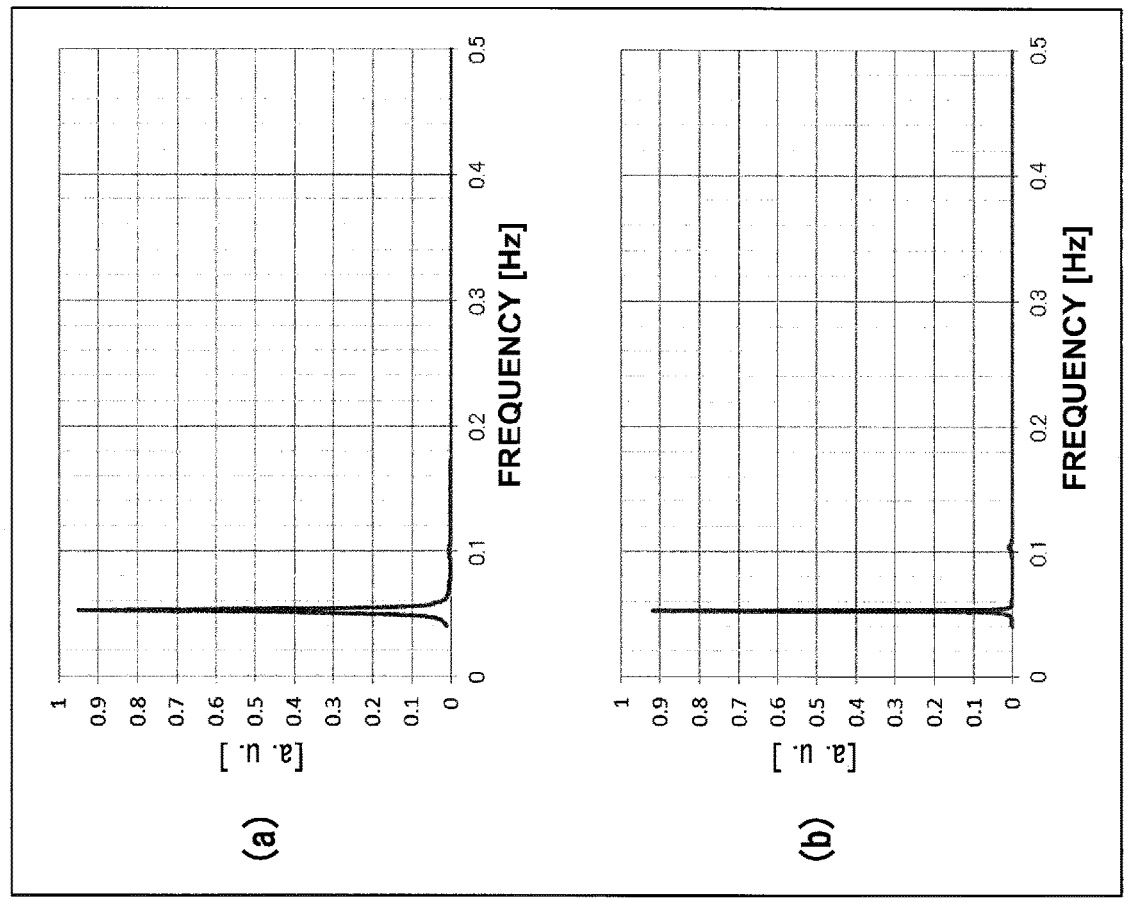
FIG. 18 shows graphs respectively showing the spectrum of the R-R intervals and the spectrum of the RS amplitudes.

The biological signal processing apparatus explained in each of the first to fifth embodiments can be implemented by a computer including a CPU (Central Processing Unit), a storage device, and an interface, and a program for controlling these hardware resources. FIG. 16 shows an example of the arrangement of this computer. The computer includes a CPU 40, a storage device 41, and an interface device (to be referred to as an I/F hereinafter) 42. The I/F 42 is connected to the electrocardiograph 1 and the like. In this computer, a program for implementing the biological signal processing method of the present invention is provided while being recorded on a recording medium such as a flexible disk, CD-ROM, DVD-ROM, or memory card, and stored in the storage device 41. The CPU 40 executes the processing described in each of the first to fifth embodiments in accordance with the program stored in the storage device 41.

INDUSTRIAL APPLICABILITY

The present invention is applicable to a technique of analyzing biological signals obtained from an electrocardiographic waveform.

EXPLANATION OF THE REFERENCE NUMERALS AND SIGNS

1 . . . electrocardiograph, 2 . . . biological signal extraction unit, 3, 3a . . . averaging processing unit, 4 . . . abnormal value determination unit, 5 . . . abnormal value processing unit, 6 . . . differential unit, 7 . . . change amount decrease determination unit, 8 . . . resampling unit, 9 . . . frequency analysis unit, 10 . . . display unit, 30 . . . reciprocal averaging processing unit, 31 . . . averaged data calculation unit

The invention claimed is:

1. A biological signal processing method causing a central processing unit to perform:
    a first step of extracting biological signals from an electrocardiographic waveform of a living body;
    a second step of calculating averaged data using time-series data of the biological signals extracted in the first step, the second step including
        performing averaging processing for values based on reciprocals of values of the time-series data of the biological signals extracted in the first step, and calculating the averaged data from a reciprocal of a value obtained by the averaging processing;
    a third step of determining, for each of the time-series data, whether the time-series data of the biological signals extracted in the first step is appropriate, the third step including
        a step of setting a normal value range by adding a first predetermined value to the average data calculated using past time-series data of the biological signals that have been determined as appropriate or by multiplying a second predetermined value and the averaged data calculated using the past time-series data of the biological signals that have been determined as appropriate, and
        a step of determining the time-series data to be determined as inappropriate when the time-series data to be determined deviates from the normal value range;
    a fourth step of performing one of deletion and interpolation of the time-series data of the biological signals determined as inappropriate in the third step;
    a fifth step of calculating a first-order differential value and a second-order differential value of each of said biological signals having undergone the processing in the fourth step; and
    a sixth step of warning that variations in the biological signals are low, when a state in which both the first-order differential value and the second-order differential value fall in a predetermined range within ±80 µV centered on 0 continues for a predetermined period of three seconds or longer.

2. The biological signal processing method according to claim 1, wherein in the second step, when performing the averaging processing of the time-series data of the biological signals extracted in the first step, the time-series data of the biological signals falling outside the predetermined range centered on the value of the averaged data calculated using time-series data that has occurred before the time-series data of the biological signals, and the time-series data of the biological signals interpolated in the fourth step are not used to calculate the averaged data.

3. The biological signal processing method according to claim 2, wherein each of the biological signals is one of an R-R interval that is a time interval between an R wave, and an immediately preceding R wave and an RS amplitude from a peak value of an R wave to a peak value of an S wave.

4. The biological signal processing method according to claim 2, further comprising:
    a seventh step of obtaining a spectrum of the biological signals by performing, by one of fast Fourier transform and a maximum entropy method, frequency analysis for the biological signals after the processing in the fourth step.

5. The biological signal processing method according claim 1, wherein the each of said biological signals is one of an R-R interval that is a time interval between an R wave and an immediately preceding R wave, and an RS amplitude from a peak value of an R wave to a peak value of an S wave.

6. The biological signal processing method according to claim 5, further comprising:
    a seventh step of obtaining a spectrum of the biological signals by performing, by one of fast Fourier transform and a maximum entropy method, frequency analysis for the biological signals after the processing in the fourth step.

7. The biological signal processing method according to claim 1, further comprising:
    a seventh step of obtaining a spectrum of the biological signals by performing, by one of fast Fourier transform and a maximum entropy method, frequency analysis for the biological signals after the processing in the fourth step.

8. The biological signal processing method according to claim 1, wherein in the second step, when performing the averaging processing of the time-series data of the biological signals extracted in the first step, the time-series data of the biological signals falling outside the predetermined range centered on the value of the averaged data calculated using time-series data that has occurred before the time-series data of the biological signals, and the time-series data of the biological signals interpolated in the fourth step are not used to calculate the averaged data.

9. The biological signal processing method according to claim 8, wherein each of the biological signals is one of an R-R interval that is a time interval between an R wave, and an immediately preceding R wave and an RS amplitude from a peak value of an R wave to a peak value of an S wave.

10. The biological signal processing method according to claim 8, further comprising:
a seventh step of obtaining a spectrum of the biological signals by performing, by one of fast Fourier transform and a maximum entropy method, frequency analysis for the biological signals after the processing in the fourth step.

11. The biological signal processing method according to claim 1, wherein each of the biological signals is one of an R-R interval that is a time interval between an R wave, and an immediately preceding R wave and an RS amplitude from a peak value of an R wave to a peak value of an S wave.

12. The biological signal processing method according to claim 1, further comprising:
a seventh step of obtaining a spectrum of the biological signals by performing, by one of fast Fourier transform and a maximum entropy method, frequency analysis for the biological signals after the processing in the fourth step.

13. A biological signal processing apparatus including a memory storing programmed instructions, a processing unit for executing programmed instructions stored in said memory and an interface coupled to external devices and said processing unit, said apparatus comprising:
biological signals extraction unit configured to extract a biological signal from an electrocardiographic waveform of a living body;
an averaging processing unit configured to calculate averaged data using time-series data of the biological signals extracted by the biological signal extraction unit, the averaging processing unit including
a reciprocal averaging processing unit configured to perform averaging processing for values based on reciprocals of values of the time-series data of the biological signals extracted by the biological signal extraction unit, and
an averaged data calculation unit configured to calculate the averaged data from a reciprocal of a value obtained by the averaging processing of the reciprocal averaging processing unit;
an abnormal value determination unit configured to determine, for each of said time-series data, whether the time-series data of the biological signals extracted by the biological signal extraction unit is appropriate, the abnormal value determination unit being configured to set a normal value range by adding a first predetermined value to the averaged data calculated using past time-series data of the biological signals that have been determined as appropriate or by multiplying a second predetermined value and the averaged data calculated using the past time-series data of the biological signals that have been determined as appropriate and
determine the time-series data to be determined as inappropriate when the time-series data to be determined deviates from the normal value range;
an abnormal value processing unit configured to perform one of deletion and interpolation of the time-series data of the biological signals determined as inappropriate by the abnormal value determination unit;
a differentiating unit configured to calculate a first-order differential value and a second-order differential value of biological signals processed by the abnormal value processing unit;
a change amount decrease determination unit configured to determine that variations in the biological signals are low, when a state in which both the first-order differential value and the second-order differential value fall in a predetermined range within ±80 µV centered on 0 continues for a predetermined period of three seconds or longer; and
a display unit configured to display a result of the determination of the change amount decrease determination unit.

14. A biological signal processing method causing a central processing unit to perform:
a first step of extracting abiological signals from an electrocardiographic waveform of a living body;
a second step of calculating averaged data using time-series data of the biological signals extracted in the first step, the second step including:
performing averaging processing for values based on reciprocals of values of the time-series data of the biological signals extracted in the first step, and
calculating the averaged data from a reciprocal of a value obtained by the averaging processing;
a third step of determining, for each of the time-series data, whether the time-series data of the biological signals extracted in the first step is appropriate, the third step including a step of setting a normal value range by multiplying a third predetermined value a variance obtained from the averaged data calculated using past time-series data of the biological signals that have been determined as appropriate, and a step of determining the time-series data to be determined as inappropriate when a variance obtained from the averaged data calculated using the time-series data to be determined and the past time-series data of the biological signals that have been determined as appropriate deviates from the normal value range;
a fourth step of performing one of deletion and interpolation of the data of the time-series biological signals determined as inappropriate in the third step;
a fifth step of calculating a first-order differential value and a second-order differential value of the biological signals having undergone the processing in the fourth step; and
a sixth step of warning that variations in the biological signals are low, when a state in which both the first-order differential value and the second-order differential value fall in a predetermined range within ±80 µV centered on 0 continues for a predetermined period of three seconds of longer.

15. A biological signal processing apparatus including a memory storing programmed instructions, a processing unit for executing programmed instructions stored in said memory and an interface coupled to external devices and said processing unit, said apparatus comprising:

biological signals extraction unit configured to extract a biological signal from an electrocardiographic waveform of a living body;

an averaging processing unit configured to calculate averaged data using time-series data of the biological signals extracted by the biological signal extraction unit, the averaging processing unit including a reciprocal averaging processing unit configured to perform averaging processing for values based on reciprocals of values of the time-series data of the biological signals extracted by the biological signal extraction unit, and an averaged data calculation unit configured to calculate the averaged data from a reciprocal of a value obtained by the averaging processing of the reciprocal averaging processing unit;

an abnormal value determination unit configured to determine, for each of the time-series data, whether the time-series data of the biological signals extracted by the biological signal extraction unit is appropriate, the abnormal value determination unit being configured to set a normal value range by multiplying a third predetermined value and a variance obtained from the averaged data calculated using past time-series data of the biological signals that have been determined as appropriate and determine the time-series data to be determined as inappropriate when a variance obtained from the averaged data calculated using the time-series data to be determined and the past time-series data of the biological signals that have been determined as appropriate deviates from the normal value range;

an abnormal value processing unit configured to perform one of deletion and interpolation of the time-series data of the biological signals determined as inappropriate by the abnormal value determination unit;

a differentiating unit configured to calculate a first-order differential value and a second-order differential value of biological signals having processed by the abnormal value processing unit;

a change amount decrease determination unit configured to determine that variations in the biological signals are low, when a state in which both the first-order differential value and the second-order differential value fall in a predetermined range within ±80 µV centered on 0 continues for a predetermined period of three seconds or longer, and a display unit configured to display a result of the determination of the change amount decrease determination unit.

* * * * *